US011541251B2

(12) United States Patent
Flynn et al.

(10) Patent No.: US 11,541,251 B2
(45) Date of Patent: Jan. 3, 2023

(54) APPARATUS AND METHOD FOR ROTATING SHIELD BRACHYTHERAPY

(71) Applicant: UNIVERSITY OF IOWA RESEARCH FOUNDATION, Iowa City, IA (US)

(72) Inventors: Ryan T. Flynn, Iowa City, IA (US); Yusung Kim, Iowa City, IA (US); Xiaodong Wu, Coralville, IA (US); Karolyn M. Hopfensperger, Iowa City, IA (US); Quentin E. Adams, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 0 days.

(21) Appl. No.: 17/277,506

(22) PCT Filed: Sep. 25, 2019

(86) PCT No.: PCT/US2019/052944
§ 371 (c)(1),
(2) Date: Mar. 18, 2021

(87) PCT Pub. No.: WO2020/068972
PCT Pub. Date: Apr. 2, 2020

(65) Prior Publication Data
US 2022/0023662 A1 Jan. 27, 2022

Related U.S. Application Data

(60) Provisional application No. 62/736,814, filed on Sep. 26, 2018.

(51) Int. Cl.
*A61N 5/10* (2006.01)

(52) U.S. Cl.
CPC .... *A61N 5/1002* (2013.01); *A61N 2005/1005* (2013.01); *A61N 2005/1094* (2013.01)

(58) Field of Classification Search
CPC .... A61N 2005/1019; A61N 2005/1024; A61N 5/1007; A61N 5/1014; A61N 5/1015;
(Continued)

(56) References Cited

U.S. PATENT DOCUMENTS 6,505,392 B1 1/2003 Liprie
6,508,755 B1 2/2003 Ravins et al.
(Continued)

FOREIGN PATENT DOCUMENTS

WO WO 2014/021947 A1 2/2014

OTHER PUBLICATIONS

International Search Report and Written Opinion for PCT/US2019/052944.

*Primary Examiner* — Samuel G Gilbert
(74) *Attorney, Agent, or Firm* — Ballard Spahr LLP

(57) ABSTRACT

Methods and systems are described for a rotating shield brachytherapy device. As disclosed herein, the rotating shield brachytherapy (RSBT) apparatus may comprise a radiation source, a drive assembly, a catheter, and an applicator. The applicator can have an outer surface and opposed proximal and distal end portions and a longitudinal axis extending along a length of the catheter. The distal end portion of the catheter can comprise one or more radiation shields and is configured to receive the radiation source. The drive assembly can be configured to engage the proximal end portion of the catheter to selectively rotate the catheter about the longitudinal axis.

20 Claims, 27 Drawing Sheets

(58) Field of Classification Search
CPC .......... A61N 5/1002; A61N 2005/1005; A61N 2005/1094
USPC ..................................................... 600/3, 6–8
See application file for complete search history.

(56) References Cited

U.S. PATENT DOCUMENTS

| | | |
|---|---|---|
| 7,530,941 B2 | 5/2009 | Munro, III et al. |
| 7,862,496 B2 | 1/2011 | Hermann et al. |
| 8,475,353 B2 | 7/2013 | Chi Sing et al. |
| 2005/0261541 A1* | 11/2005 | Henderson ........... A61N 5/1027 600/7 |
| 2007/0191667 A1* | 8/2007 | Lubock ................ A61N 5/1015 600/3 |
| 2014/0187849 A1 | 7/2014 | Bakker et al. |
| 2017/0173362 A1 | 6/2017 | Lamoureux et al. |
| 2020/0246634 A1* | 8/2020 | Lim ....................... A61B 6/107 |

\* cited by examiner

ASSEMBLING A ROTATING SHIELD BRACHYTHERAPY APPARATUS

1110 — USING A ROTATING SHIELD BRACHYTHERAPY APPARATUS

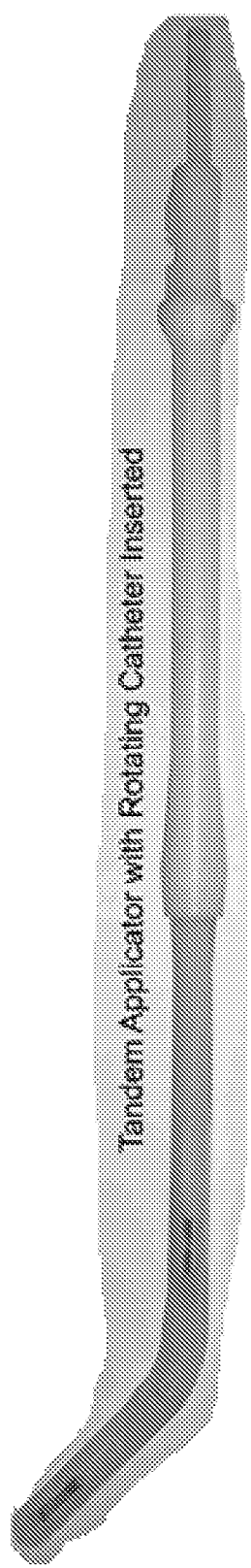
FIG. 14C Tandem Applicator with Rotating Catheter Inserted
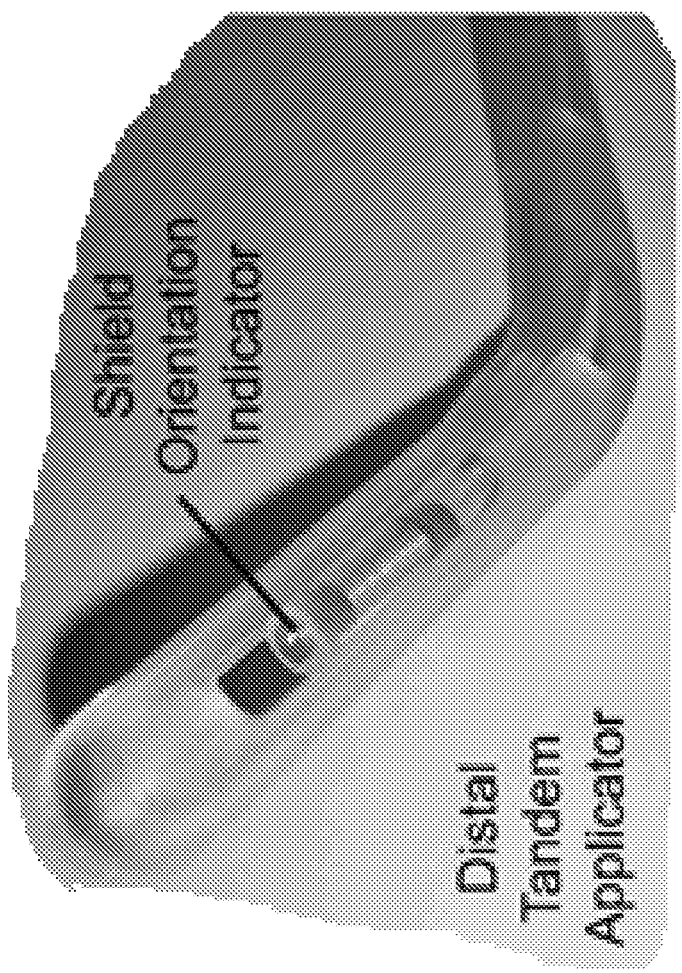
FIG. 14D Distal Tandem Applicator, Shield Orientation Indicator

APPARATUS AND METHOD FOR ROTATING SHIELD BRACHYTHERAPY

CROSS REFERENCE TO RELATED APPLICATIONS

This is a U.S. National Phase Application of International Application No. PCT/US2019/052944, filed Sep. 25, 2019, which claims priority to and the benefit of the filing date of U.S. Provisional Patent Application No. 62/736,814, filed Sep. 26, 2018, which applications are hereby incorporated by reference herein in their entireties.

STATEMENT OF GOVERNMENT SUPPORT

This invention was made with government support under grant numbers EB020665 and CA210737 awarded by the National Institutes of Health. The Government has certain rights in this invention.

FIELD

This disclosure relates to an apparatus and method for delivering intracavitary (IC) rotating shield brachytherapy (RSBT). The apparatus and method can be used for the treatment of cancer.

BACKGROUND

The present disclosure overcomes the limitations of intracavitary and interstitial (IC/IS) high-dose-rate brachytherapy (HDR-BT) for treating cancer by providing an IC-only approach with the potential to replace the IC/IS approach. The current disclosure has several advantages that are intended to address the impediments of IC/IS HDR-BT. HDR-BT is typically delivered with a radioisotope on a wire, which is translated throughout an intrauterine tube-shaped IC applicator. Cervical cancer tumors are often laterally extended and non-symmetric, and are also surrounded by bladder, bowel, rectum, sigmoid colon, and vaginal tissues. With this geometric problem, the radiation dose that can be delivered to the tumor is often limited by the presence of the bladder, rectum, and sigmoid colon, reducing the chances that the tumor can be controlled.

SUMMARY

It is to be understood that both the following general description and the following detailed description are exemplary and explanatory only and are not restrictive. Methods and systems are described for a rotating shield brachytherapy device. As disclosed herein, the rotating shield brachytherapy (RSBT) apparatus may comprise a radiation source, a drive assembly, a catheter, and an applicator. The applicator can have an outer surface, opposed proximal and distal end portions, and a longitudinal axis extending along a length of the catheter. The distal end portion of the catheter can comprise one or more radiation shields and is configured to receive the radiation source. The drive assembly can be configured to engage the proximal end portion of the catheter to selectively rotate the catheter about the longitudinal axis. The applicator can be configured to have an inner surface, an outer surface, and a central axis along a length of the applicator. The inner surface of the applicator can define a bore configured to receive at least a portion of the catheter. In an aspect, upon receipt of the catheter within the bore of the applicator and rotation of the catheter by the drive assembly, the inner surface of the applicator can be configured to engage the outer surface of the catheter in a manner sufficient to cause advancement of the catheter in a distal direction along the length of the applicator. Further, methods of assembling and using the disclosed apparatus are also described herein.

This summary is not intended to identify critical or essential features of the disclosure, but merely to summarize certain features and variations thereof. Other details and features will be described in the sections that follow.

BRIEF DESCRIPTION OF THE DRAWINGS

FIG. 10 is a flowchart of an exemplary method for assembling a rotating shield brachytherapy apparatus as disclosed herein.

FIG. 11 is a flowchart of an exemplary method for using a rotating shield brachytherapy apparatus as disclosed herein.

FIG. 14C is a side view of the rotating catheter of FIG. 14B inserted into the applicator of FIG. 14A.

FIG. 14D is a detail view of a distal end of the applicator and rotating catheter of FIG. 14C.

DETAILED DESCRIPTION

Figure 1:
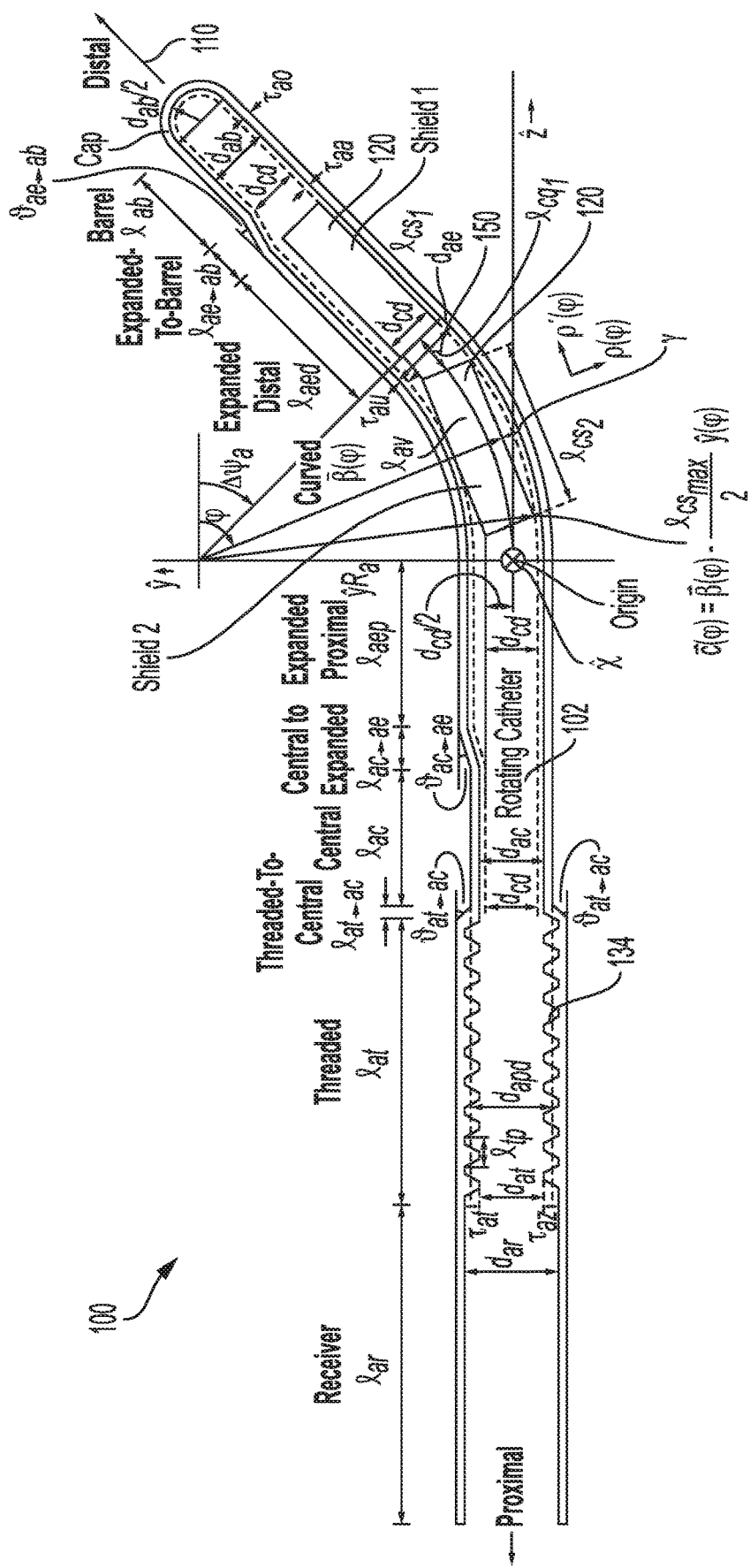
FIG. 1 illustrates a side view schematic of an exemplary apparatus as disclosed herein.
Figure 2A:
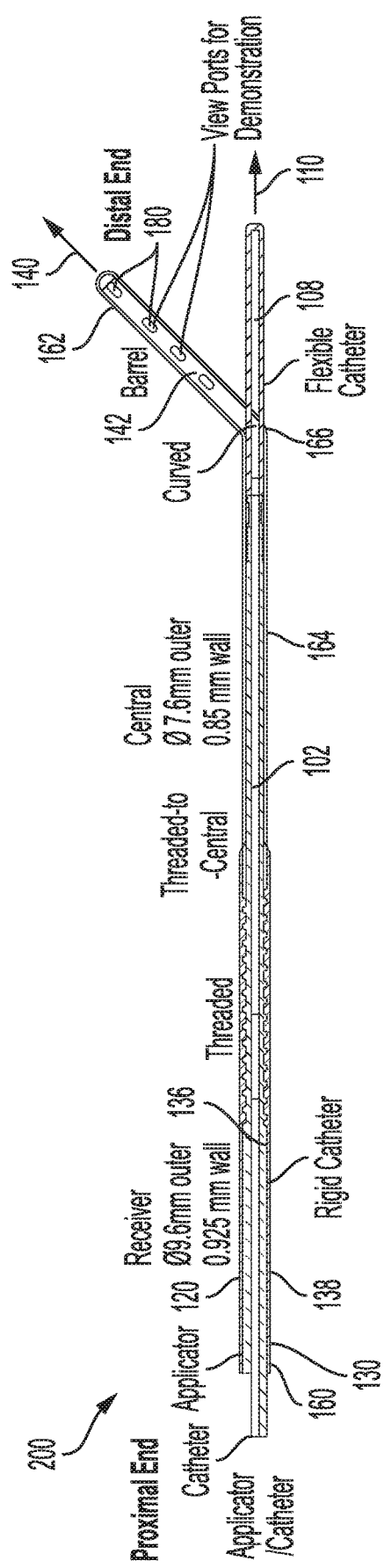
FIG. 2A illustrates a sectional side view of an exemplary apparatus as disclosed herein.
Figure 2B:
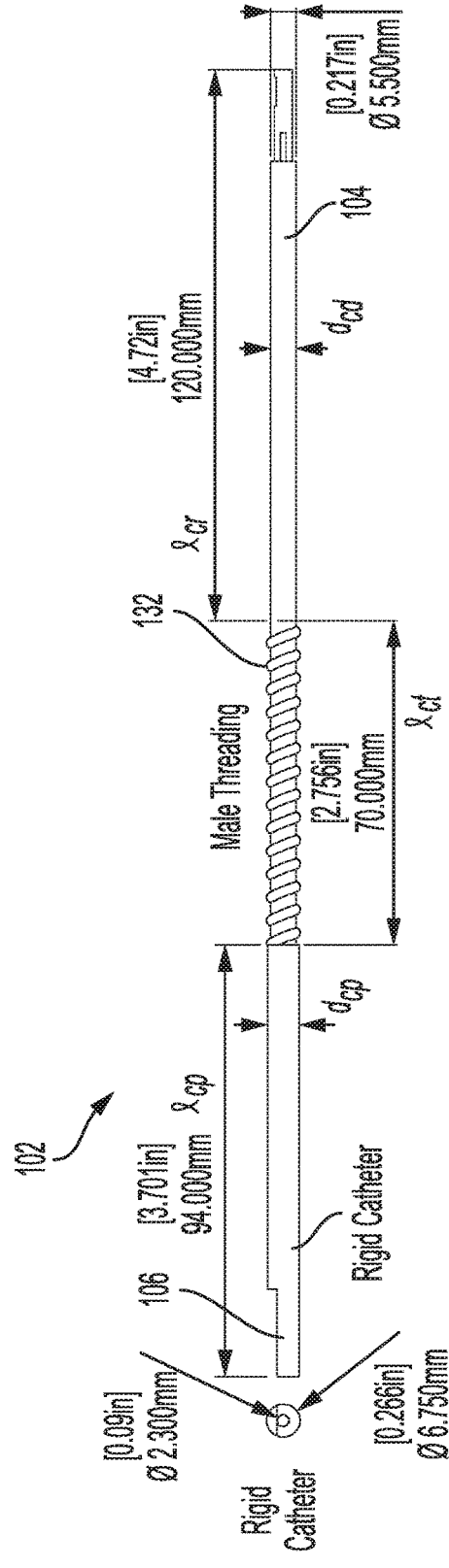
FIG. 2B illustrates a rigid catheter of the exemplary apparatus as in FIG. 2A
Figure 2C:
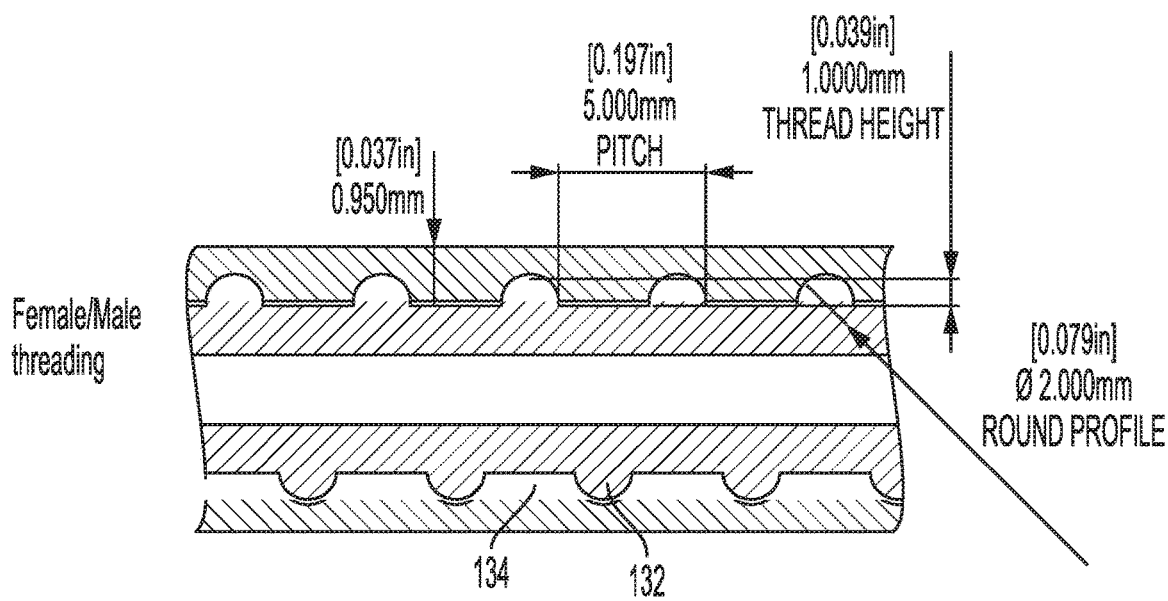
FIG. 2C illustrates a detail view of FIG. 2A showing threading between the catheter and an applicator.
Figure 2D:
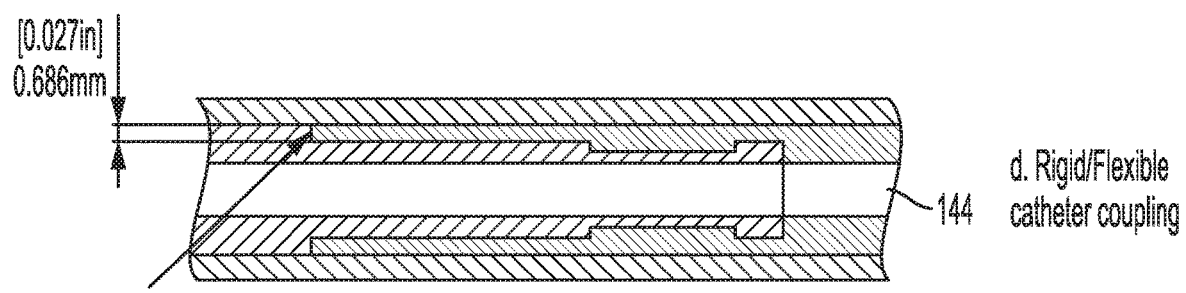
FIG. 2D illustrates a detail view of FIG. 2A showing a coupling between the rigid catheter and a flexible catheter.
Figure 2E:
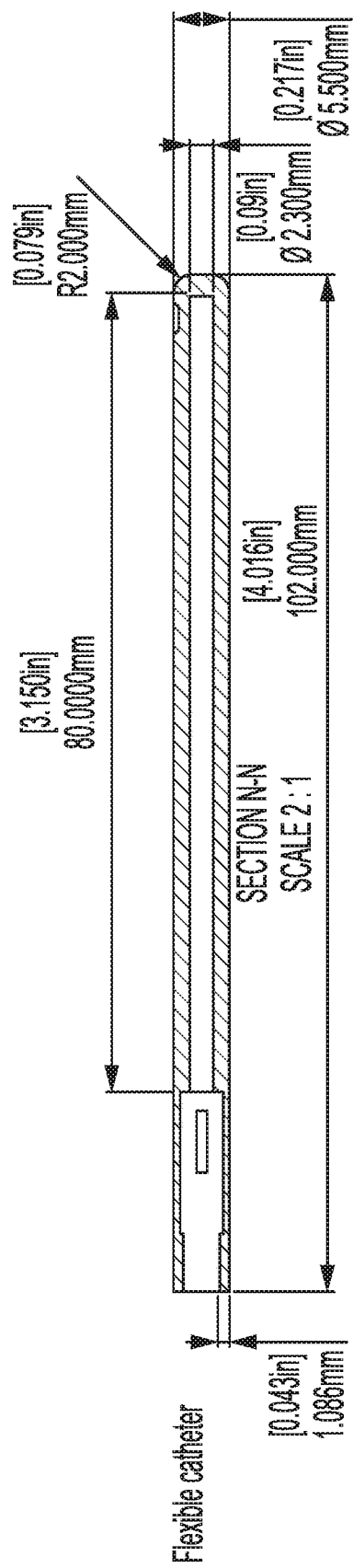
FIG. 2E illustrates a cross sectional view of the flexible catheter as in FIG. 2A

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" comprise plural referents unless the context clearly dictates otherwise. Thus, for example, reference to "a shield" can comprise two or more such shields unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The steps of all methods described herein can be performed in any suitable order unless otherwise specified herein or clearly indicated by context. The use of any and all examples or exemplary language (e.g., "such as") herein is intended merely to better illuminate the invention and not to place a limitation on the scope of the invention, unless otherwise indicated by the claims. Nothing in the specification should be construed as indicating any non-claimed element as essential to the practice of the invention. Ranges can be expressed herein as from "about" one particular value to "about" another particular value. Such an expression is intended to include a range from the one particular value to the other particular value, as well as ranges including variations in the particular values.

The term "subject" refers to an individual, and can include humans as well as other animals. The term "subject" does not denote a particular age or sex, and can include animals of either sex and of any age.

As used herein, the terms "optional" or "optionally" mean that the subsequently described event or circumstance can or cannot occur, and that the description comprises instances where said event or circumstance occurs and instances where it does not.

As used herein, in some optional aspects, unless the context indicates otherwise, when values are approximated by use of the term "substantially" or "about," it is contemplated that values within up to 20%, up to 15%, up to 10%, up to 5%, or up to 1% (above or below) of the particular value can be included within the scope of those aspects. In further optional aspects, the included values can include the particular value modified by the term "substantially" or "about." For example, it is contemplated that the term "substantially parallel" can include aspects in which the recited elements are parallel.

The word "or" as used herein means any one member of a particular list and also comprises any combination of members of that list.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal configuration. "Such as" is not used in a restrictive sense, but for explanatory purposes.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

This detailed description may refer to a given entity performing some action. It should be understood that this language may in some cases mean that a system (e.g., a computer) owned and/or controlled by the given entity is actually performing the action.

The apparatus, systems, and methods described herein can produce radiation dose distributions with superior target conformity to those deliverable with conventional IC high-dose-rate brachytherapy (HDR-BT), and better target conformity to those delivered with combined intracavitary and interstitial (IC/IS) HDR-BT. The apparatus, systems, and methods described herein can comprise a tube-shaped applicator through which a catheter containing a partially-shielded radiation source travels to deliver a high radiation dose to pathologic tissue surrounding or adjacent to the applicator. The applicator and rotating catheter have interlocking female and male threads, similar to a nut and a bolt. The apparatus, systems, and methods can comprise an applicator-mounted drive system that rotates the catheter to produce a collimated radiation beam that travels along a helical path inside the target tissue. The source dwell times at all points along the helix are calculated with a treatment planning system that optimizes the tradeoff between target dose conformity and sensitive normal tissue sparing.

FIGS. 1 and 2A-2E illustrate an exemplary apparatus 100. In an aspect, the apparatus 100 is a rotating shield brachytherapy (RSBT) apparatus. In an aspect, the apparatus 100 can comprise an IC applicator 130 and a rotating catheter 102. The rotating catheter 102 can have an outer surface 104, a proximal end portion 106 and an opposed distal end portion 108, and a longitudinal axis 110 extending along its length. The longitudinal axis 110 can be centered in cross sections of the catheter along its length. In an aspect, the rotating catheter 102 can be inserted through the IC applicator 130. The IC applicator 130 can have an inner surface 136, an outer surface 138, and a central axis 140 along the length of the applicator. The inner surface 136 of the applicator 130 can define a bore 142 that can be configured to receive at least a portion of the catheter 102. In an aspect, the rotating catheter 102 can comprise a partially-shielded radiation source 122 (FIG. 3A-3D) that travels in a helical pattern to enable the delivery of tumor-conformal dose distributions. Rotational force can be applied to the rotating catheter 102 by a motorized drive system (e.g., the apparatus 500, 600, and 700 of FIGS. 5, 6, and 7, respectively). In an aspect, when the catheter is rotated, the catheter can advance through the applicator due to mechanical engagement between male threads 132 and female helical threads 134 on the catheter and applicator, respectively.

The RSBT apparatus can comprise a radiation source, a drive assembly, a catheter, and an applicator. The catheter can have an outer surface and opposed proximal and distal end portions. The catheter can have and a longitudinal axis extending along a length of the catheter. The distal end portion of the catheter can comprise one or more radiation shields. The catheter can be configured to receive the radiation source. The radiation source can be any radioactive material. In an aspect, the radiation source can be Ytterbium-169 ($^{169}$Yb). Some additional non-limiting examples of radiation sources are Cobalt-56 ($^{56}$Co), Cobalt-57 ($^{57}$Co), Cobalt-58 ($^{58}$Co), Cobalt-60 ($^{60}$Bo) Zinc-65 ($^{65}$Zn), Technetium-99m ($^{99m}$Tc), Palladium-103 ($^{103}$Pd), Cadmium-109 ($^{109}$Cd), Iodine-125 ($^{125}$I), Caesium-131 ($^{131}$Cs), Samarium-145 ($^{145}$Sm), Gadolinium ($^{153}$Gd), Thulium-170 ($^{170}$Tm), Tungsten-187 ($^{187}$W), Iridium-192 ($^{192}$Ir), Gold-198 ($^{198}$Au), Californium-252 ($^{252}$Cf), or an electronic brachytherapy source. The one or more radiation shields can comprise radiation-blocking material such as stainless steel, platinum, tungsten, tungsten carbide, uranium, osmium, iridium, gold, lead, bismuth, iron, molybdenum, silver, tungsten, osmium, and the like. The one or more radiation shields can define at least one radiation window 170 (FIGS. 3A-3D) that allows radiation (e.g., from the radiation source) to exit the catheter.

Figure 3A:
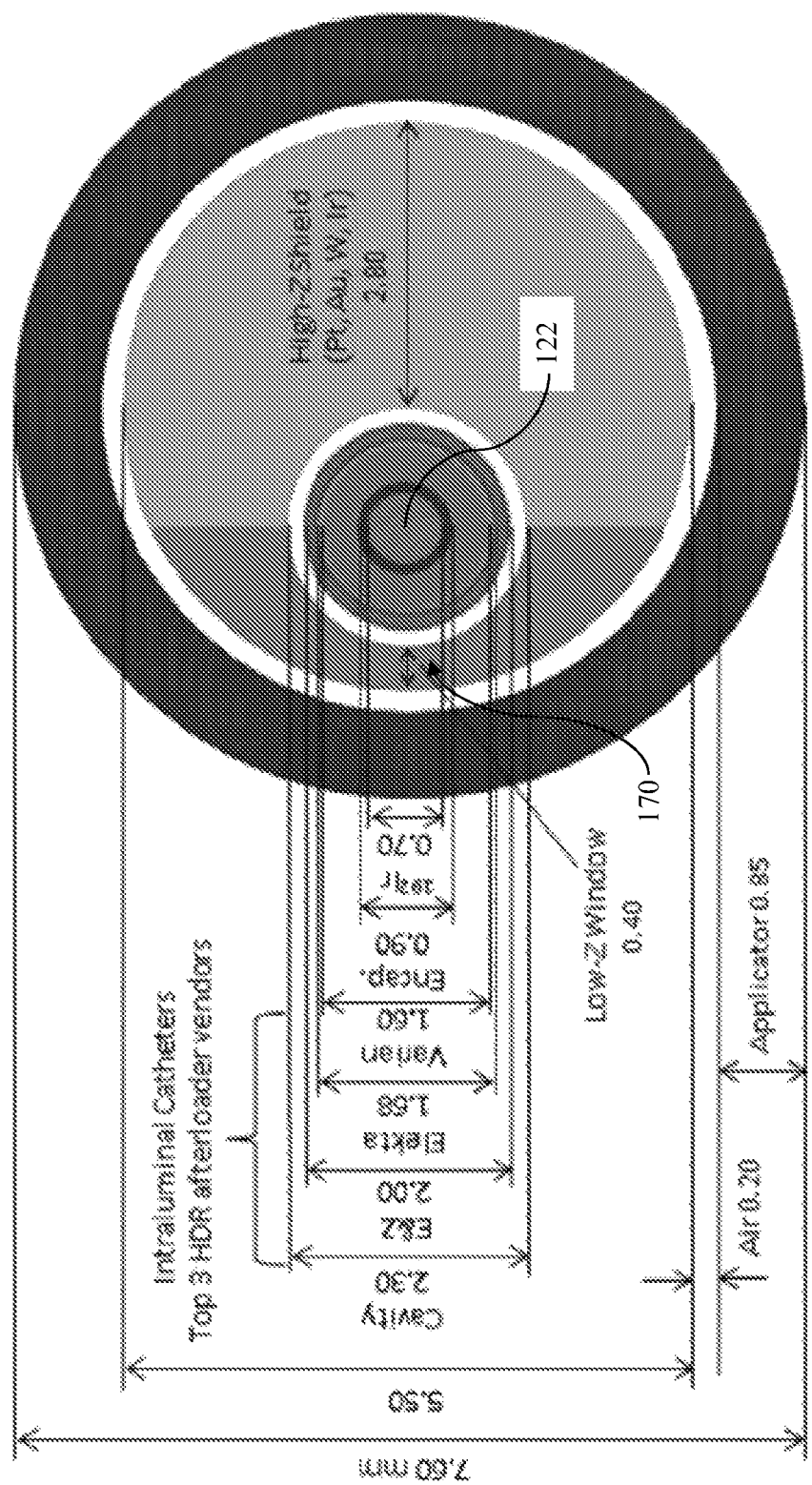
FIG. 3A illustrates a cross section of an exemplary apparatus as disclosed herein.
Figure 3B:
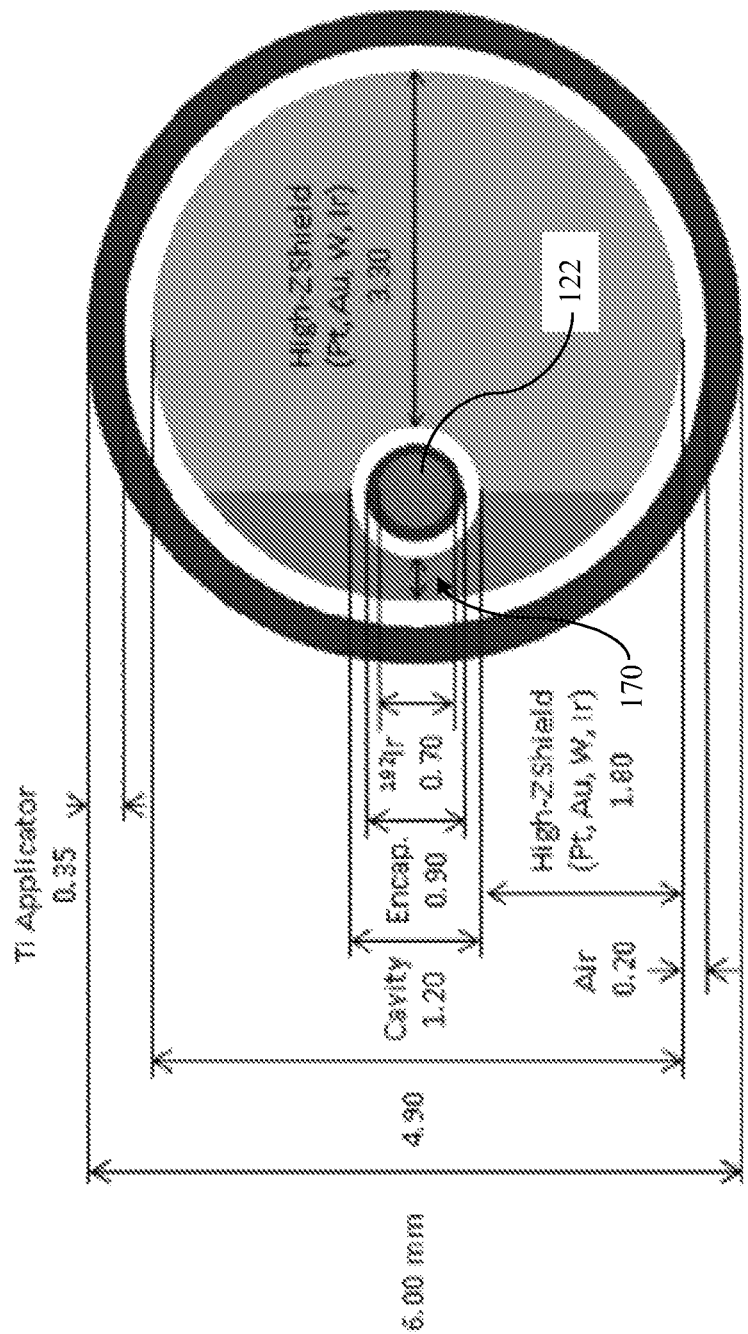
FIG. 3B illustrates a cross section of an exemplary apparatus as disclosed herein.
Figure 3C:
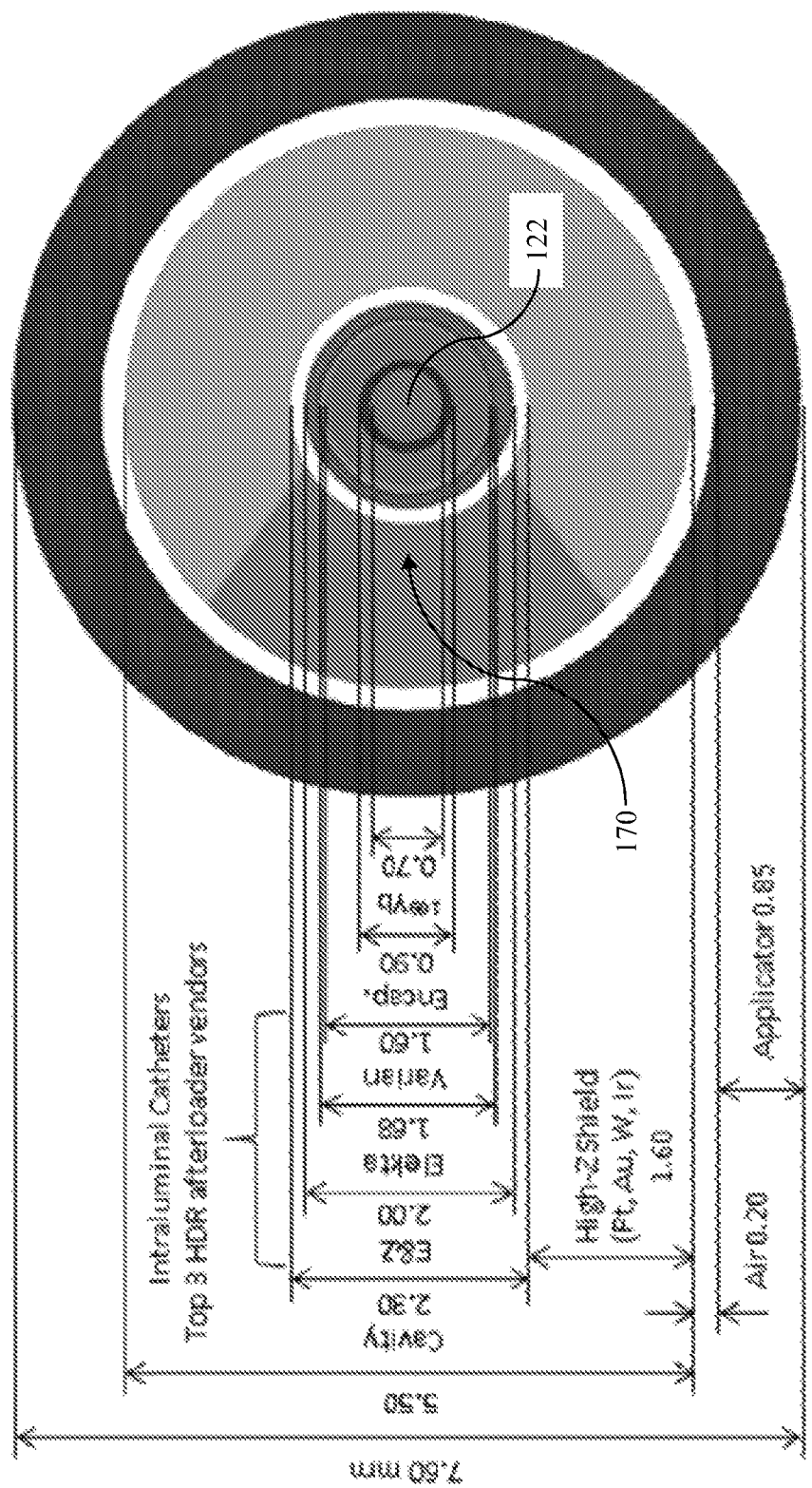
FIG. 3C illustrates a cross section of an exemplary apparatus as disclosed herein.
Figure 3D:
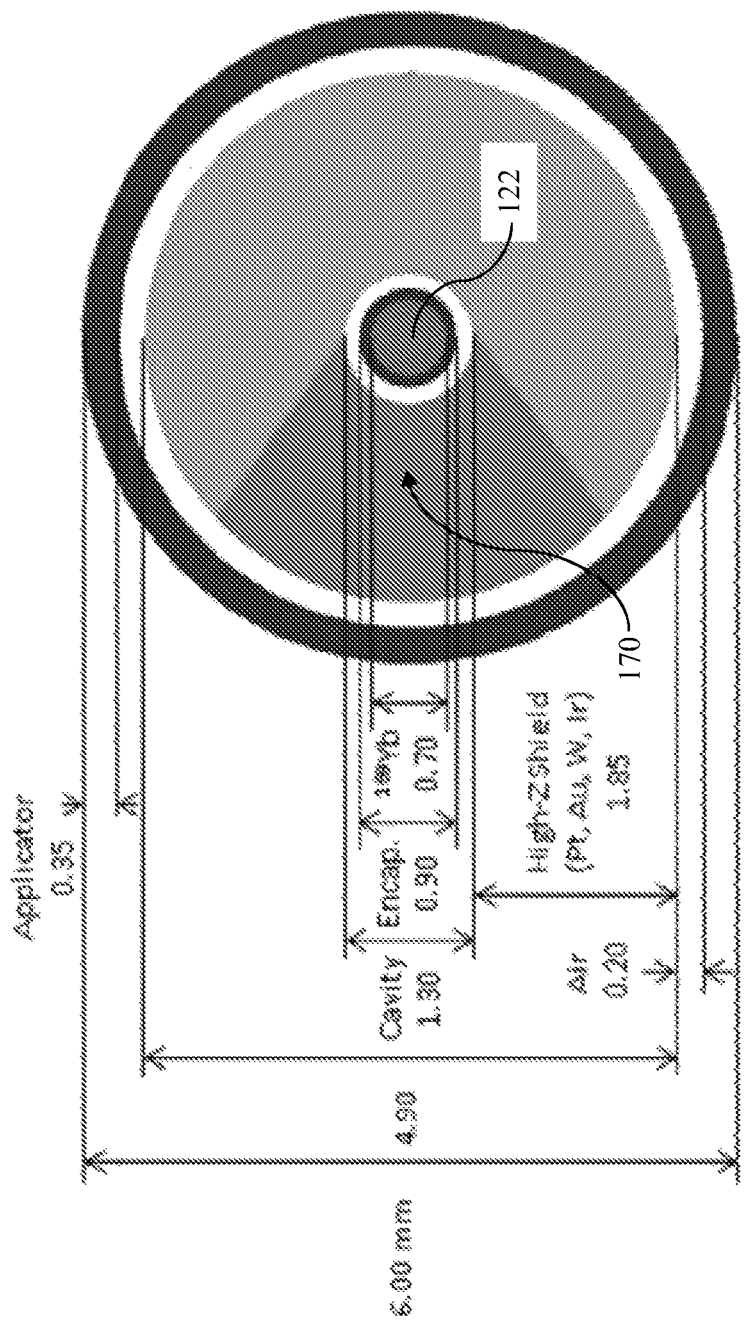
FIG. 3D illustrates a cross section of an exemplary apparatus as disclosed herein.

In an aspect, the distal end portion of the catheter can comprise at least one axial position 150 along longitudinal axis of the catheter at which no radiation shield is present. In an aspect, the distal end portion of the catheter can be sufficiently flexible to traverse a curved portion of the applicator and sufficiently rigid to transfer rotational motion to the one or more radiation shields. In an aspect, the catheter can define a lumen 144 (FIG. 2D) that is configured to receive the radiation source. In an aspect, the lumen can be radially offset from the longitudinal axis of the catheter, as shown in FIGS. 3A and 3B. In an aspect, the lumen is aligned or substantially aligned with the longitudinal axis of the catheter, as shown in FIGS. 3C and 3D.

The drive assembly can be configured to engage the proximal end portion of the catheter to selectively rotate the catheter about the longitudinal axis. The drive assembly can be configured for attachment to a proximal end portion of the applicator. In an aspect, the drive assembly can comprise a locking mechanism for the catheter that prevents longitudinal motion and allows rotational motion of the catheter. The drive assembly can comprise one or more rotational motors that are mechanically coupled to the catheter. In an aspect, the drive assembly comprises a plurality of rotation motors, and at least one rotational motor of the plurality of rotational motors is redundant.

The applicator can have an inner surface, an outer surface, and a central axis along a length of the applicator. In an aspect, the applicator can be at least partially curved. In an aspect, the applicator can be straight, and/or substantially straight. The inner surface of the applicator can define a bore configured to receive at least a portion of the catheter. In an aspect, upon receipt of the catheter within the bore of the applicator and rotation of the catheter by the drive assembly, the inner surface of the applicator can be configured to engage the outer surface of the catheter in a manner sufficient to cause advancement of the catheter in a distal direction along the length of the applicator. In an aspect, the inner surface of the applicator and the outer surface of the catheter can be at least partially helically threaded. The helically threaded portions of the inner surface of the applicator can be configured to complementarily engage helically threaded portions of the outer surface of the catheter to permit advancement of the catheter in a distal direction along the length of the applicator.

In an aspect, the applicator can have a proximal end portion 160 and an opposed distal end portion 162, a central portion positioned 164 axially between the proximal and distal end portions, and a curved portion 166 positioned axially between the central portion and the distal end portion. In an aspect, the bore of the applicator has a variable diameter that increases within the curved portion. In an aspect, the applicator can be an interstitial applicator and/or an intracavitary applicator. In an aspect, the applicator comprises one or more optically transparent or translucent portions 180. In an aspect, the optically transparent or translucent portions of the applicator can comprise internal or external markings that are configured to permit measurement of depth and/or angular location of the catheter. In an aspect, the internal or external markings are configured to permit measurement of an axial location of the catheter and/or a radiation source wire within the catheter.

Figure 13:
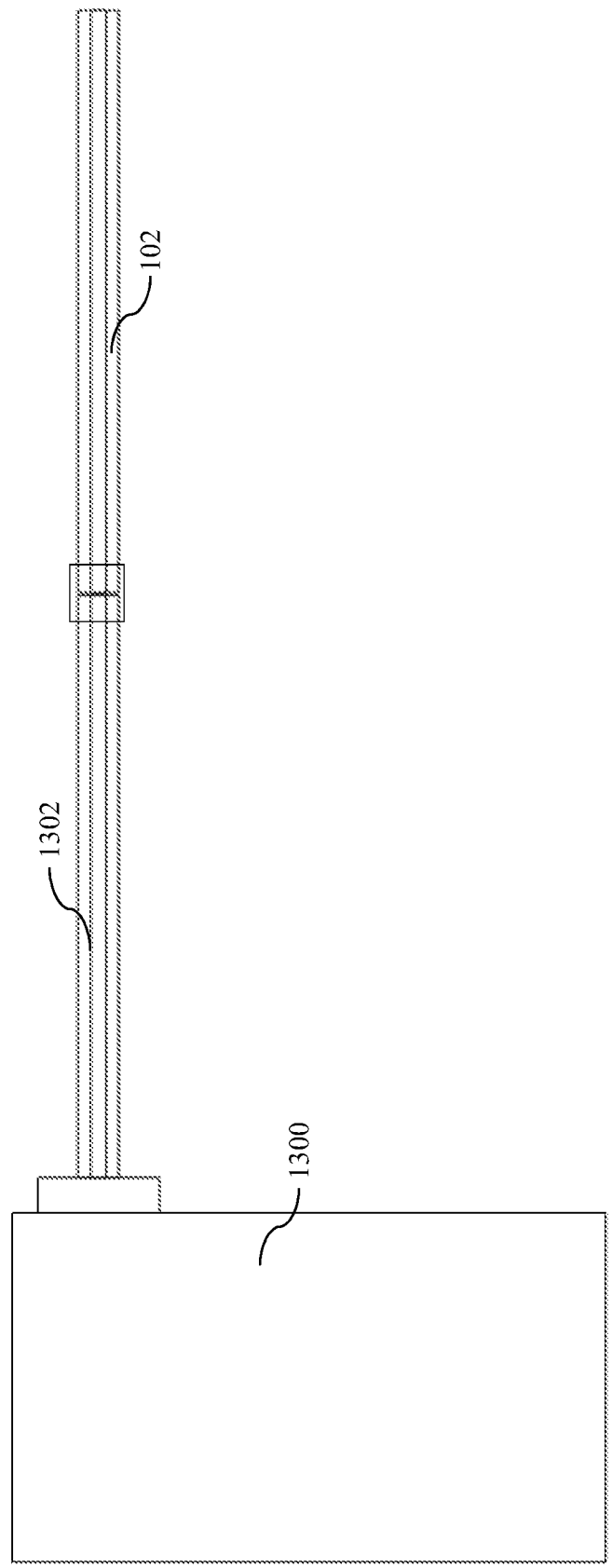
FIG. 13 is a schematic of an exemplary apparatus comprising an afterloader.
Figure 14A:
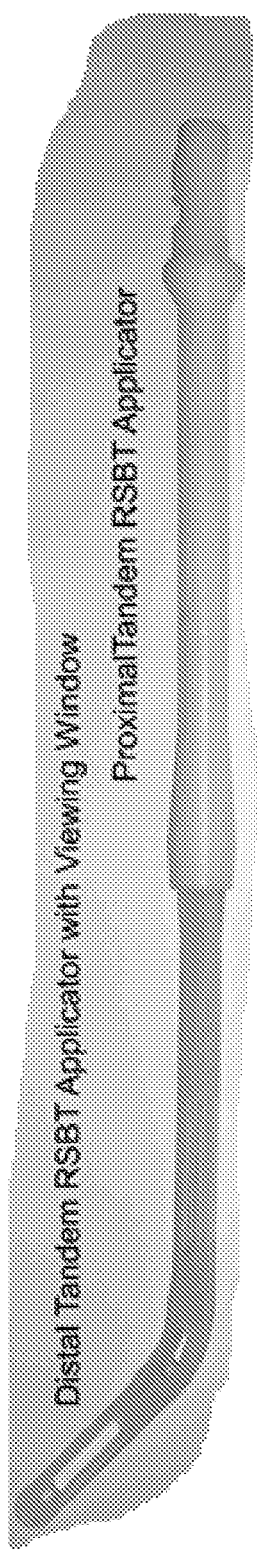
FIG. 14A is a side view of an applicator in accordance with embodiments disclosed herein.
Figure 14B:
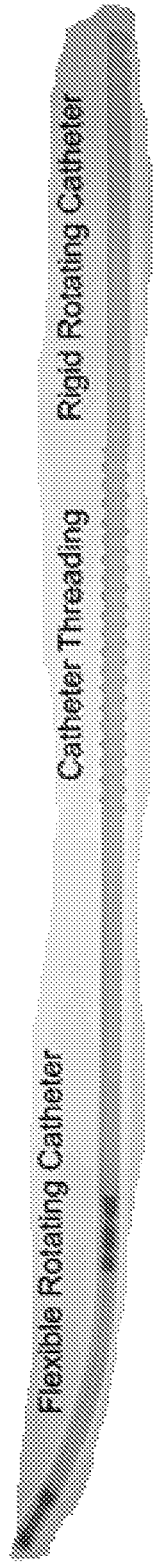
FIG. 14B is a side view of a rotating catheter in accordance with embodiments disclosed herein.

Referring to FIG. 13, in an aspect, the RSBT apparatus can further comprise a second catheter 1302 coupled to an afterloader 1300. In an aspect, the catheter defines a lumen that is configured to receive the radiation source, and the second catheter and afterloader are configured to deliver the radiation source to the lumen of the catheter. In an aspect, the catheter defines a lumen that is directly connected to the afterloader, and the catheter can be configured to receive the radiation source through the afterloader.

Components of the RSBT apparatus are shown in FIG. 1, with the nomenclature associated with those two components listed in Table 1. The applicator has distal and proximal ends. In an aspect, the distal end can be protruding from the patient and the proximal end can be inserted into the patient. In an aspect, the apparatus 100 can comprise six sections: (1) a receiver into which the rotating catheter can be inserted, (2) a threaded section with female threads, (3) a central section, (4) a proximal expanded section, which can be expanded to enable unobstructed travel of the shield or shields, (5) an expandable distal section, and (6) the barrel section, through which most of the radiation dose can be delivered. There are also transitions between major sections and a hemispherical cap at the distal end. Applicator and rotating catheter lengths are denoted with $\ell_a$ and $\ell_c$, respectively, diameters with $d_a$ and $d_c$, respectively, with additional letters in the subscripts denoting the applicator or rotating catheter sections. For example, $\ell_{ac}$ denotes the length ($\ell$) of the applicator's (subscript a) central (subscript c) section.

TABLE 1

Exemplary Applicator and rotating catheter nomenclature.

| Name | Symbol | Description |
|---|---|---|
| Applicator | | |
| Radius of curvature | $R_a$ | |
| Angle | $\Delta\psi_a$ | |
| Applicator coordinate system unit vectors | $\hat{x}, \hat{y}, \hat{z}$ | $\hat{x}$ is patient left to right, $\hat{y}$ is floor to ceiling, $\hat{z}$ is proximal-to-distal |
| Angle of shield inside applicator | $\varphi$ | Increases from $+\hat{z}$ to $-\hat{y}$ |
| Shield coordinate system | $\hat{r}(\varphi), \hat{r}'(\varphi)$ | $\hat{r}(\varphi) = \hat{z}\cos\varphi - \hat{y}\sin\varphi$, $\hat{r}'(\varphi) = \hat{z}\sin\varphi + \hat{y}\cos\varphi$ |
| Lengths | | |
| Receiver | $\ell_{ar}$ | |
| Threaded | $\ell_{at}$ | |
| Threaded to central transition | $\ell_{at \to ac}$ | |
| Central | $\ell_{ac}$ | |
| Central to expanded transition | $\ell_{ac \to ae}$ | |
| Proximal shield expansion | $\ell_{aep}$ | |
| Curve | $\ell_{av}$ | $\ell_{av} = R_a(\pi/2 - \Delta\psi_a)$ |
| Distal shield expansion | $\ell_{aed}$ | |
| Distal shield expansion to distal transition | $\ell_{ae \to ab}$ | |
| Barrel | $\ell_{ab}$ | |
| Thread pitch | $\ell_{tp}$ | |
| Total applicator length along bore axis, not including end cap | $\ell_a$ | $\ell_a = \ell_{ar} + \ell_{at} + \ell_{at \to ac} + \ell_{ac} + \ell_{ac \to ae} + \ell_{aep} + \ell_{av} + \ell_{aed} + \ell_{ae \to ab} + \ell_{ab}$ |
| Inner diameters | | |
| Receiver | $d_{ar}$ | Also major thread pitch diameter |
| Threaded | $d_{at}$ | Also minor thread pitch diameter |
| Threaded pitch diameter | $d_{apd}$ | $d_{apd} = d_{at} + \tau_{at}$ |
| Central | $d_{ac}$ | |

TABLE 1-continued

Exemplary Applicator and rotating catheter nomenclature.

| Name | Symbol | Description |
|---|---|---|
| Expanded for shield travel | $d_{ae}$ | |
| Barrel | $d_{ab}$ | |
| Thicknesses | | |
| Air between catheter and applicator wall | $\tau_{aa}$ | |
| Thread | $\tau_{at}$ | |
| Outer | $\tau_{ao}$ | Applicator thickness |
| Angles | | |
| Threaded to central transition | $\vartheta_{at \to ac}$ | Example angle: 45° |
| Central to proximal expansion transition | $\vartheta_{ac \to ae}$ | Example angle: 15° |
| Transition from distal expansion to distal | $\vartheta_{ae \to ab}$ | Example angle: 15° |
| Catheter | | |
| Lengths | | |
| Non-threaded proximal | $\ell_{cp}$ | |
| Threaded | $\ell_{ct}$ | |
| Central | $\ell_{cr}$ | |
| Shield i (i = 1, . . . , $N_s$) | $\ell_{cs_i}$ | The shield at i = 1 is the most distal |
| Inter-shield space i (i = 1, . . . , $N_s$ − 1) | $\ell_{cq_i}$ | Space i is between shields i and i + 1 |
| Maximum shield length | $\ell_{cs_{max}}$ | Maximum of $\ell_{cs_i}$ over i = 1, . . . , $N_s$ |
| Diameters | | |
| Proximal | $d_{cp}$ | |
| Distal | $d_{cd}$ | Also shield diameter |

In an aspect, the rotating catheter can comprise multiple shields. The shields can be serial, and each shield can have a different emission angle, as indicated in FIG. 1. In an aspect, inter-shield space can be present in order to ensure that the distal rotating catheter has adequate flexibility to traverse the curved portion of the applicator. In an aspect, one or more locations along the rotating catheter can have no shield. By not shielding the entire catheter, radially-symmetric dose rate distributions can be provided in the locations that are not shield. For example, the distal end or between the shields may not be shielded.

In an aspect, the rotating catheter can comprise one or more partial radiation shields. The rotating catheter, by comprising one or more partial radiation shields, can allow the radiation source to be configured to dwell within the shields that are needed for a given patient and the rotating catheter is positioned throughout the applicator as needed. In an aspect, the rotating catheter can be located for each of the one or more shields. In an aspect, the shields can be positioned in the rotating catheter such that the emission angles decrease in the proximal-to-distal direction. By doing so, dose conformity may be ensured.

In an aspect, the RSBT apparatus can use a plurality of rotating catheters 102. Each rotating catheter may comprise one or more partial radiation shields with varying emission angles. Optionally, at least one of the rotating catheters 102 can define a position along its length without a partial shield that can provide radially symmetric dose distributions when the radiation source is positioned at such a location. In this way, select dosage patterns can be provided along the entire length of the applicator. It should be understood that for a single catheter having a plurality of shields (e.g., as shown in FIG. 1), a proximal shield cannot extend to the distal end of the applicator (due to the presence of more distally positioned shields within the catheter). Thus, for example, if the proximal shield emits radiation through a 180 degree window, and the distal shield emits radiation through a 45 degree window, the single catheter cannot emit radiation through the 180 degree window at the distal end of the applicator (due to the presence of the distal shield at the distal end of the applicator). In using a first catheter and then a second catheter, wherein the first catheter comprises a shield having a 45 degree window at a distal end of the first catheter, and the second catheter comprises a shield having a 180 degree window at the distal end of the second catheter, each shield can extend to the distal end of the applicator, thereby enabling a dosage pattern that can be difficult or impossible to provide if using a single catheter.

The rigid shield or shields can travel through the applicator unobstructed without getting physically stuck inside. The inner dimensions of the curved portion of the applicator can therefore be greater than the dimensions required for a straight applicator. As shown in FIG. 1, the inner diameter of the applicator, $d_{ae}$, in the proximal expanded, curved, and distal expanded regions of the applicator can be determined by accounting for the air thickness, $\tau_{aa}$, the catheter diameter and shield diameter, $d_{cd}$, and the maximum shield length, $\ell_{cs_{max}}$. In an aspect, $C(R_a)$ can be the circle of radius $R_a$, which is in the yz plane, is centered at $\hat{y}R_a$, and defines the central axis of the curved portion of the applicator. In an aspect, $P(\varphi)$ can be the plane rotated about unit vector $\hat{x}$ by angle $\varphi$, which includes the point $\hat{y}R$ and axially bisects shield 2 as shown in FIG. 1. In an aspect, the vector $\vec{\beta}(\varphi)$ can start at point $\hat{y}R_a$ and can end on the furthest point from $\hat{y}R_a$ that is on the shield and on the intersection of the yz plane and $P(\varphi)$. The vector $\vec{\beta}(\varphi)$ can have direction $\hat{r}(\varphi)$ and magnitude β. In an aspect, r̂'(φ) can be the unit vector in the yz plane, which is rotated −90 degrees relative to r̂(φ)[r̂'(φ)=r̂(φ−90°)]. In an aspect, $$\vec{c}(\varphi) = \vec{\beta}(\varphi) - \frac{\ell_{cs_{max}}}{2}\hat{r}'(\varphi)$$

can be the vector difference between point ŷR$_a$ and the far corner of the shield in the P(φ) plane. In an aspect, as the shield moves through the curved part of the applicator, $\vec{c}$ (φ) can be constrained to at least a distance τ$_{aa}$ from the inner wall of the applicator, which can be achieved by the following:

$$\|\vec{c}(\varphi)\|^2 = \left\|\vec{\beta}(\varphi) - \frac{\ell_{cs_{max}}}{2}\hat{r}'(\varphi)\right\|^2 = \left(R_a + \frac{d_{cd}}{2}\right)^2, \quad (1)$$

which can be rewritten as:

$$\beta^2 + \frac{\ell_{cs_{max}}^2}{4} = \left(R_a + \frac{d_{cd}}{2}\right)^2 \quad (2)$$

and solved for β as:

$$\beta = \sqrt{\left(R_a + \frac{d_{cd}}{2}\right)^2 - \frac{\ell_{cs_{max}}^2}{4}}. \quad (3)$$

The distance between $\vec{\beta}$ (φ) and the inner applicator wall, γ, along direction r̂(φ) can be calculated as:

$$\gamma = R_a + \frac{d_{cd}}{2} + \tau_{aa} - \beta = R_a + \frac{d_{cd}}{2} + \tau_{aa} - \sqrt{\left(R_a + \frac{d_{cd}}{2}\right)^2 - \frac{\ell_{cs_{max}}^2}{4}}, \quad (4)$$

and therefore the applicator inner diameter in the widened region, d$_{ae}$, is:

$$d_{ae} = \tau_{aa} + d_{cd} + \gamma = R + 2\tau_{aa} + \frac{3d_{cd}}{2} - \sqrt{\left(R_a + \frac{d_{cd}}{2}\right)^2 - \frac{\ell_{cs_{max}}^2}{4}}. \quad (5)$$

For example, an R$_a$ of 15 mm, d$_{cd}$ of 5.5 mm, τ$_{aa}$ of 0.2 mm, and $\ell_{cs_{max}}$ of 11.6 mm, we obtain an applicator inner diameter, d$_{ae}$, of 6.9 mm. This value only needs to apply to the curved portion of the applicator. For applicator wall thicknesses of 0.35 mm and 0.85 mm, the total applicator thicknesses in the curved region are 7.6 mm and 8.6 mm, respectively. As will be appreciated by one skilled in the art, the aforementioned values are used for ease of explanation and are merely exemplary. The various dimensions of the applicator can be any size and are not restricted by the aforementioned exemplary embodiments.

FIGS. 2A-2E illustrate an exemplary apparatus 200, which can optionally include the features disclosed and described with respect to apparatus 100. In an aspect, the apparatus 200 is a rotating shield brachytherapy (RSBT) apparatus. In an aspect, the apparatus 200 can include an applicator and a rotating catheter pair. The apparatus 200 can be a rotating catheter (FIG. 2A and FIG. 2B) designed to have a rigid component and a flexible component. The rigid component contains a proximal end with a D-shaped cross section to which rotational force is applied, enabling the rigid component of the rotating catheter to be easily rotated. In an aspect, the catheter can be rotated by a mechanical drive system. In another aspect, the catheter can be rotated without a mechanical drive system. The rigid component transfers the applied rotation to the flexible component. In an aspect, the rigid component transfers the applied rotation to the flexible component via a coupling. The coupling can be constructed with an over-molding process in which the flexible component is molded directly onto the rigid component. In an aspect, the flexible rotating catheter component can be constructed of a material such as thermoplastic elastomer (TPE) or thermoplastic polyurethane (TPU).

FIGS. 3A-3D each illustrate a cross section of an exemplary apparatus 100 having an applicator barrel 300. The applicator barrel 300 can be the apparatus 100 of FIG. 1 and/or the apparatus 200 of FIGS. 2A-2E.

According to one aspect, a system can comprise a plurality of rotating catheters. For example, according to some aspects, a system can comprise a plurality of rotating catheters, 102, each with one or more radiation shields 120, or one or more locations without a partial shield that can provide radially symmetric dose distributions when the radiation source is positioned at such locations. According to one aspect, each rotating catheter can have a shield at the distal end or in the distal portion. The plurality of rotating catheters can optionally be used to deliver treatment one rotating catheter at a time. Optionally, each rotating catheter can comprise a shield that is configured to travel to the distal end, or substantially the distal end or proximate the distal end, of the applicator. This configuration can be advantageous relative to a single rotating catheter with a plurality of shields since, with multiple rotating catheters, any partial shield, or an unshielded source dwell position, can be positioned at the distal-most location within the applicator. With a single rotating catheter with multiple shields, shields (120) with indices (as further disclosed herein) that are greater than 1 (FIG. 1) cannot travel to the distal end of the applicator and therefore may not be able to be used to deliver the dose distribution about the distal-most length of the applicator. For example, if a single rotating catheter with a 45° distal (index 1) shield and a 180° proximal (index 2) shield is used, then the 180° shield will never be physically located at the distal-most length of the applicator, and the corresponding dose distribution about the distal-most length of the applicator must be accomplished primarily with the 45° shield. Thus the dose distribution about the distal-most length of the applicator may not be delivered as efficiently as it would if access to both the 45° and 180° emission angle shields was available. Two separate rotating catheters, one with a 45° emission angle and one with a 180° angle, can be used to address this issue. It may also be advantageous to use a single rotating catheter with a single partial shield to deliver a treatment, depending on the patient's anatomy.

Figure 4A:
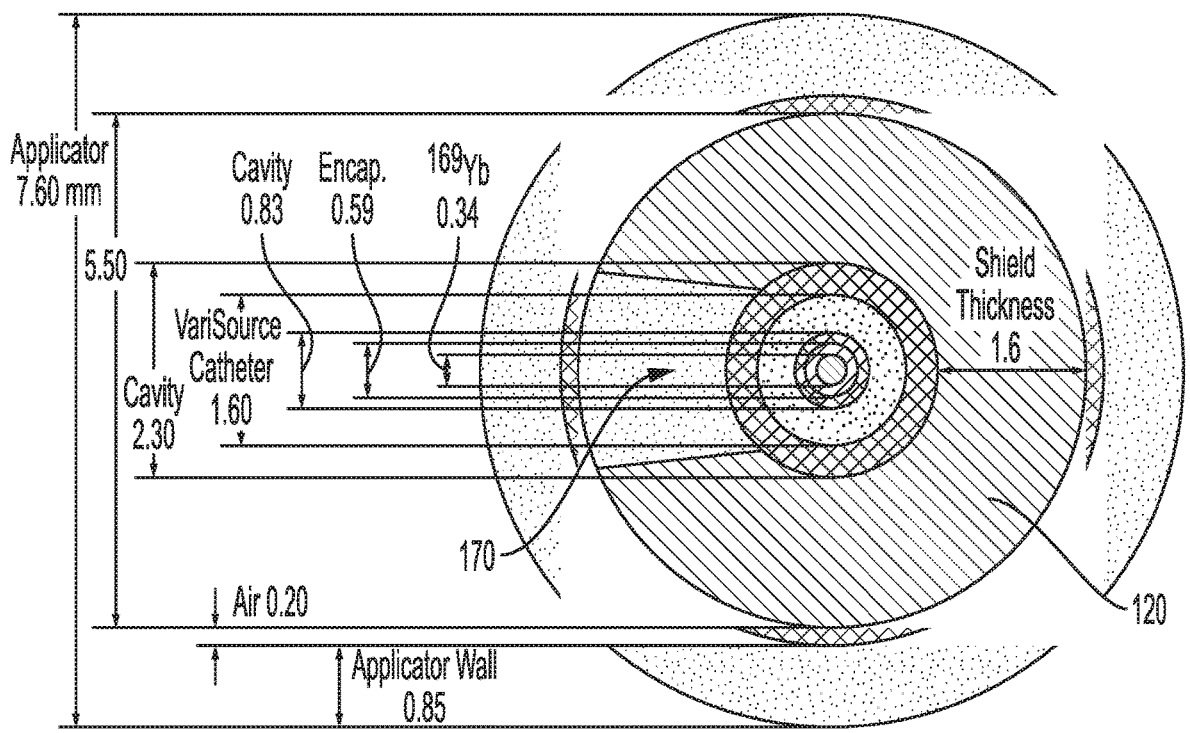
FIG. 4A illustrates an axial view of an exemplary apparatus as disclosed herein.
Figure 4B:
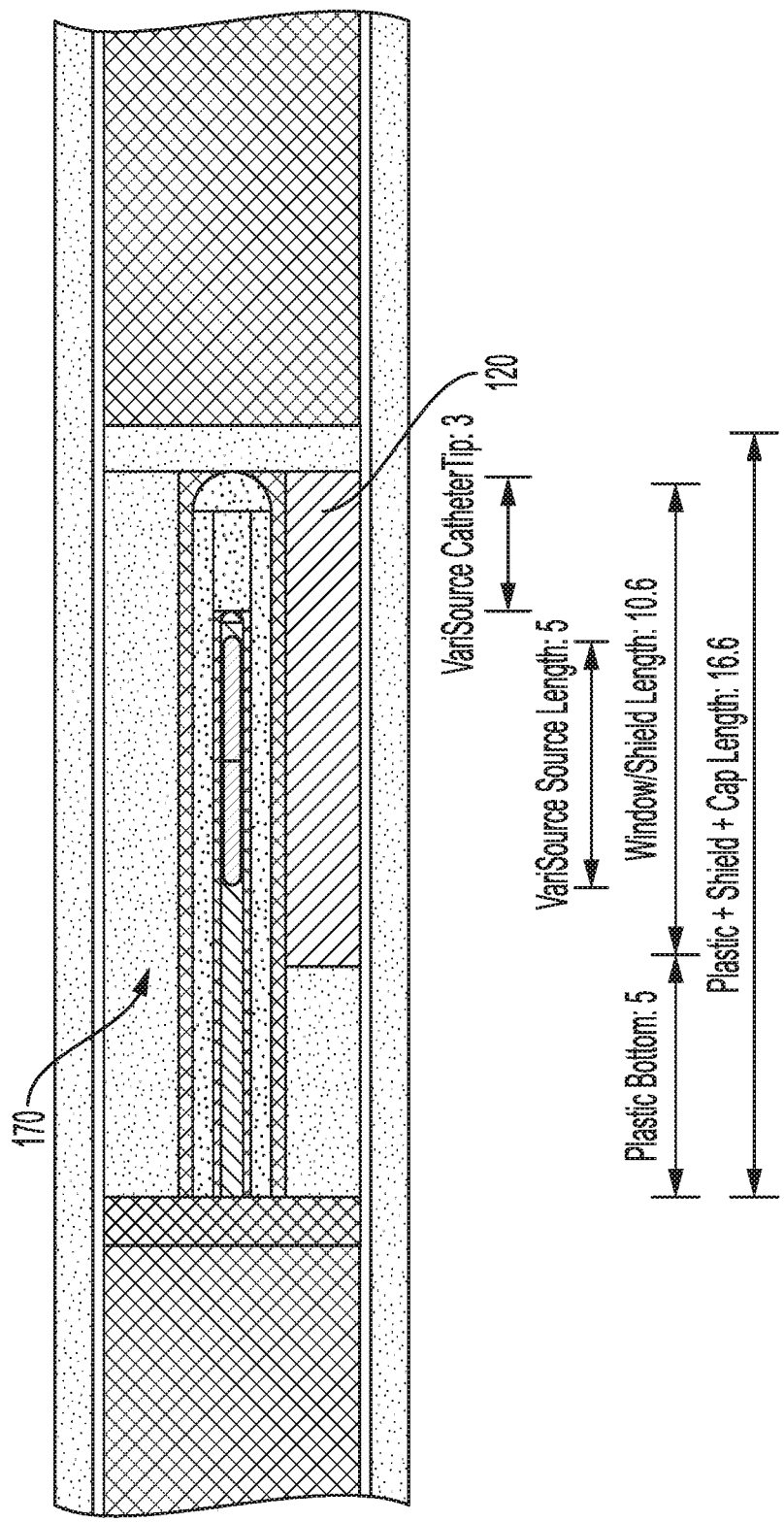
FIG. 4B illustrates a coronal view of an exemplary apparatus as disclosed herein.
Figure 4C:
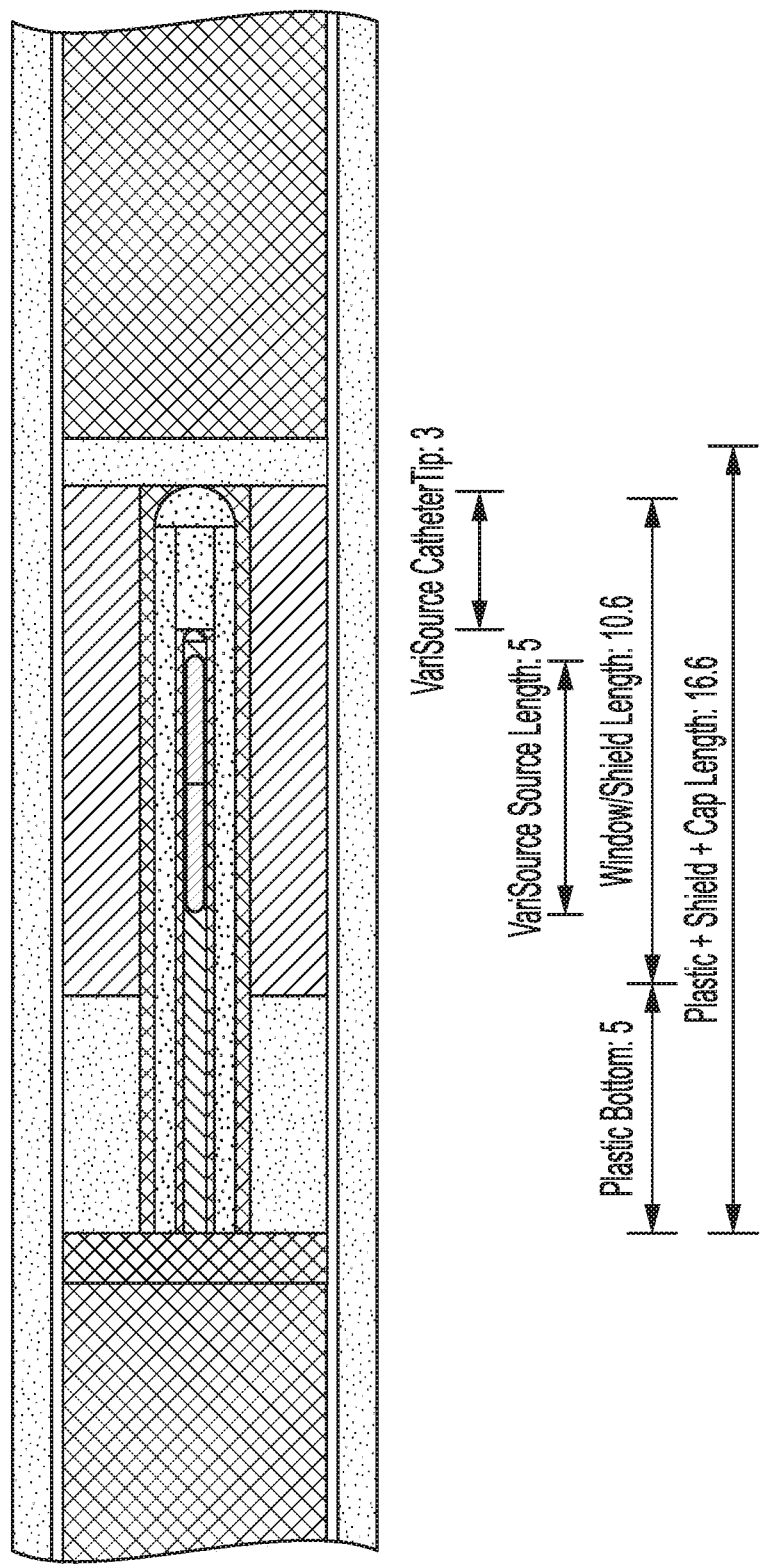
FIG. 4C illustrates a sagittal view of an exemplary apparatus as disclosed herein.
Figure 4D:
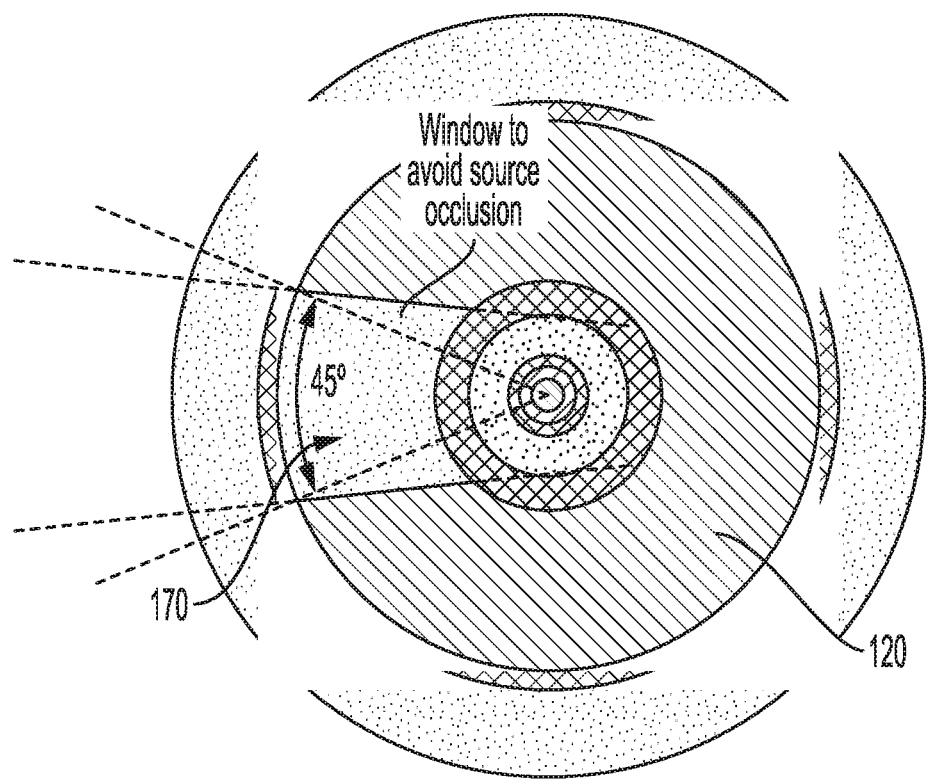
FIG. 4D illustrates an axial view of an exemplary apparatus as disclosed herein.
Figure 4E:
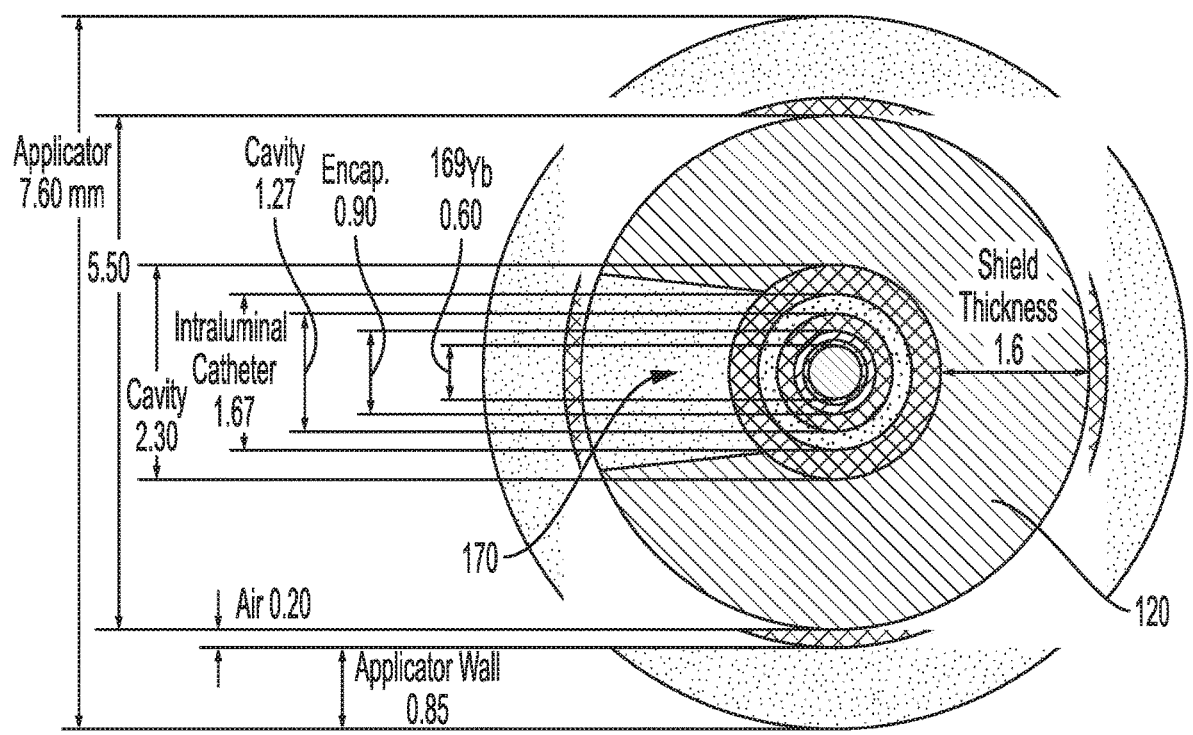
FIG. 4E illustrates an axial view of an exemplary apparatus as disclosed herein.
Figure 4F:
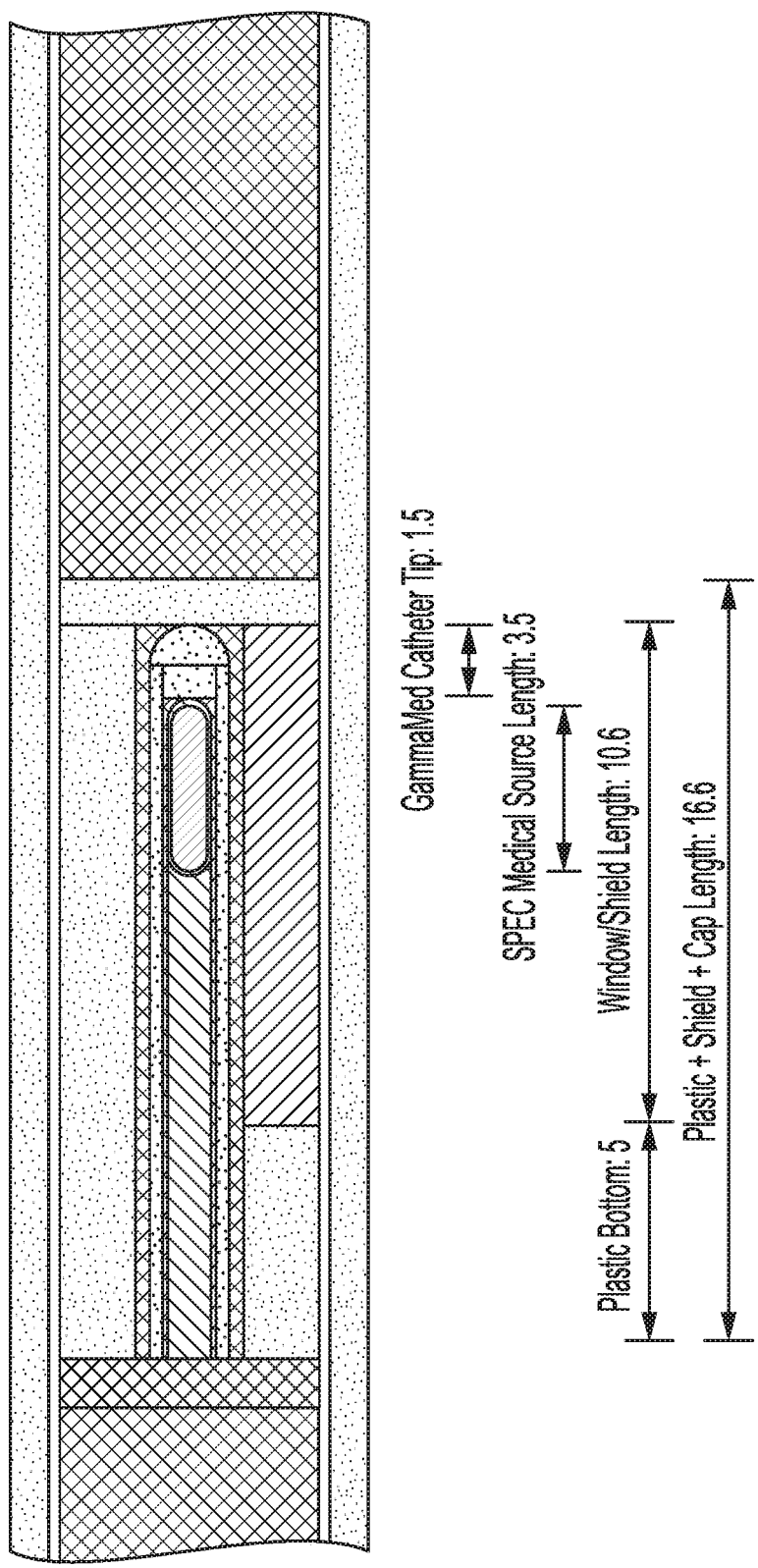
FIG. 4F illustrates a coronal view of an exemplary apparatus as disclosed herein.
Figure 4G:
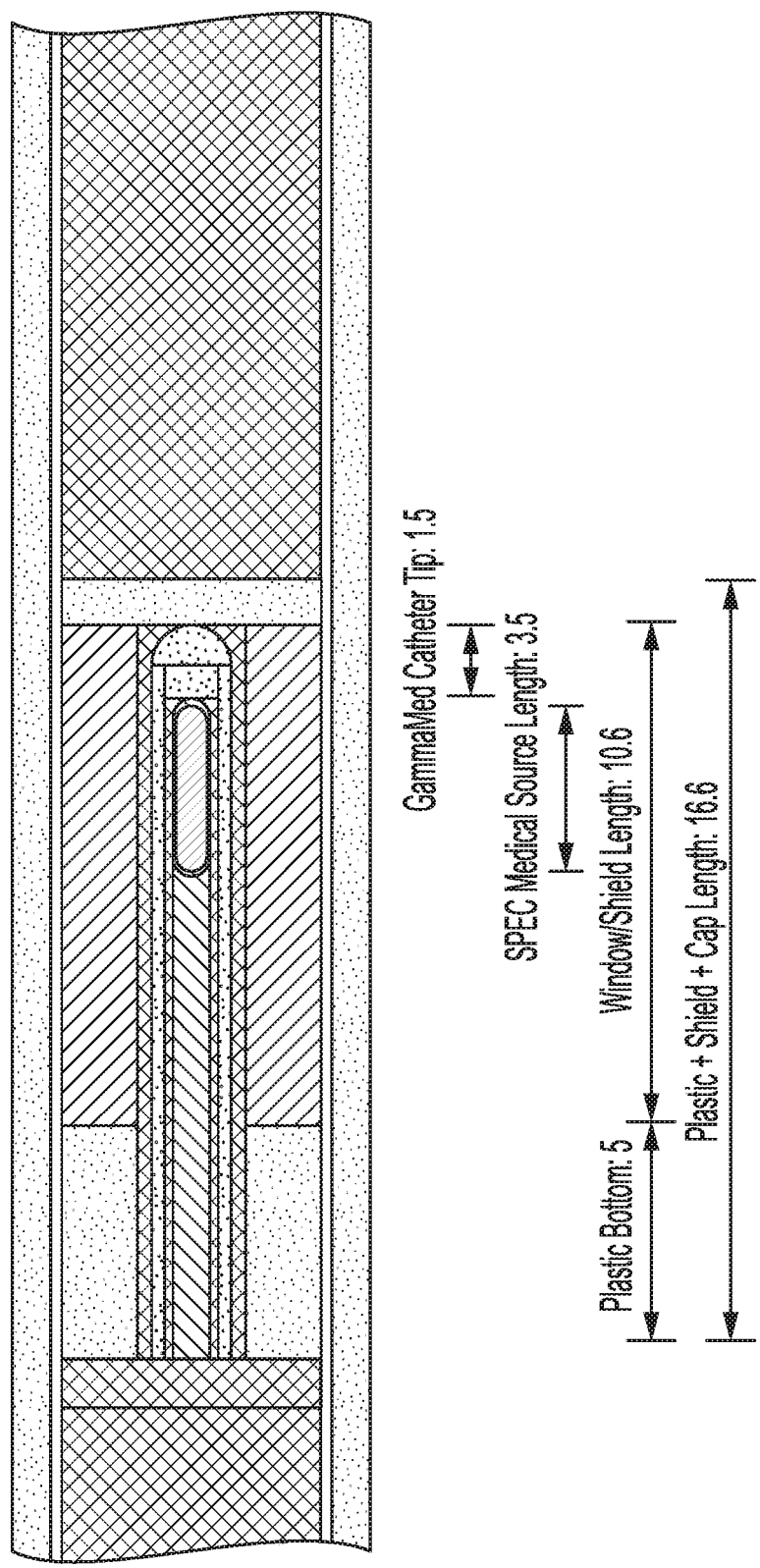
FIG. 4G illustrates a sagittal view of an exemplary apparatus as disclosed herein.
Figure 4H:
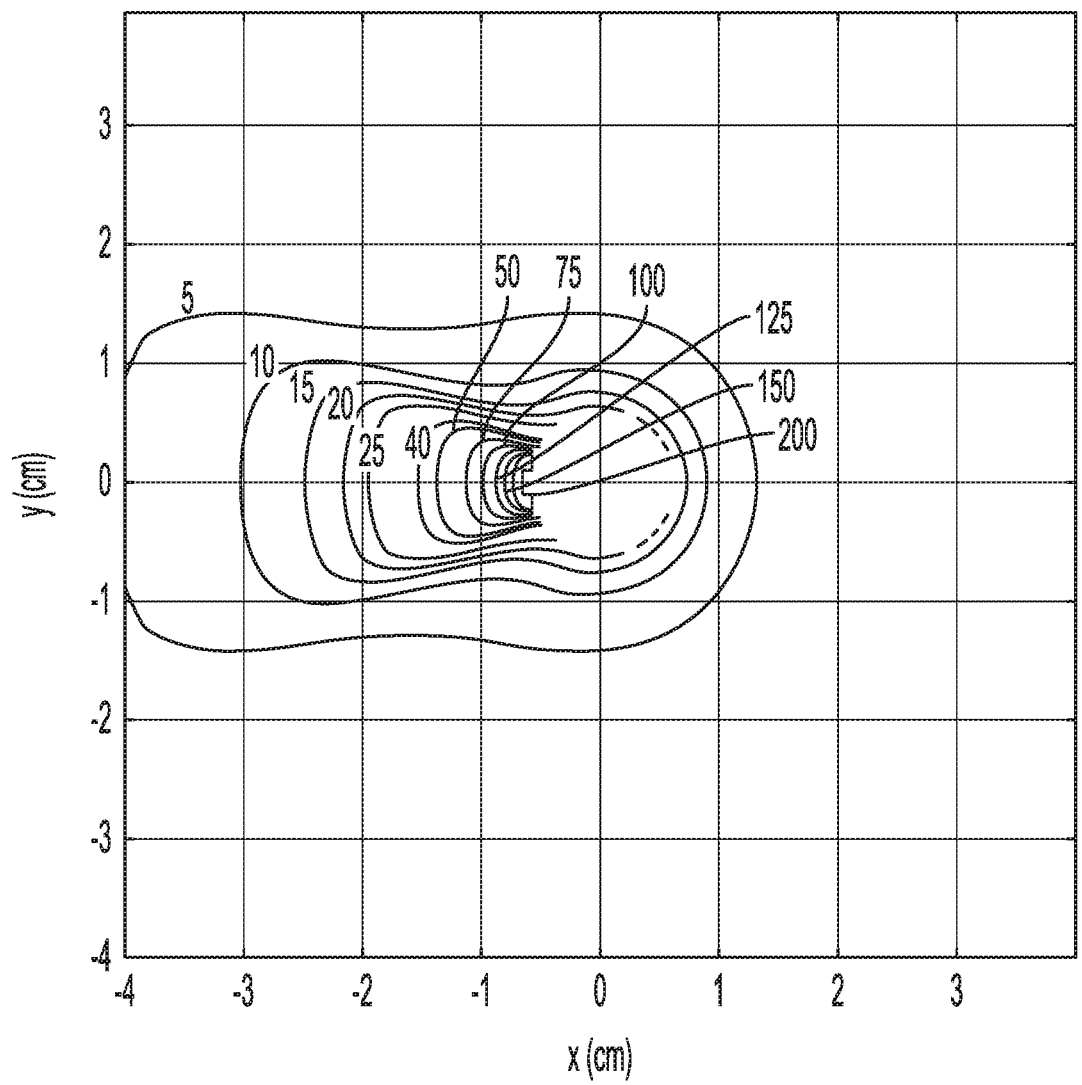
FIG. 4H illustrates a radiation intensity map of an exemplary apparatus as disclosed herein.

FIGS. 4A-4E illustrates an axial and coronal view of an exemplary apparatus 400. As shown, FIG. 4A comprises an axial view, FIG. 4B shows sagittal nad coronal views, and FIGS. 4C-4D show emission window definition for a partially-shielded source. In an aspect, the partially shield can be a $^{169}$Yb radiation source with a 45° emission angle. While a 45° emission angle is described for ease of explanation, a person skilled in the art would appreciate that any emission angle can be used (e.g., 1°, 5°, 90°, 120°, 234°, etc.) and should not be limited to the aforementioned aspect. In an aspect, the $^{169}$Yb radiation source can be based on the VARIAN VARISOURCE high-dose-rate brachytherapy source with the VARIAN STANDARD CATHETER. (d) Axial view and (e) sagittal/coronal views of the same catheter/shield from (a)-(c) except with a SPEC MEDICAL M23 $^{169}$Yb radiation source (similar dimensions as GAMMAMEDPLUS) and a VARIAN Intraluminal catheter. (f) Dose rate distribution from (d)-(e). The apparatus 400 can be the apparatus 100 of FIG. 1 and/or the apparatus 200 of FIGS. 2A-2E.

Figure 5:
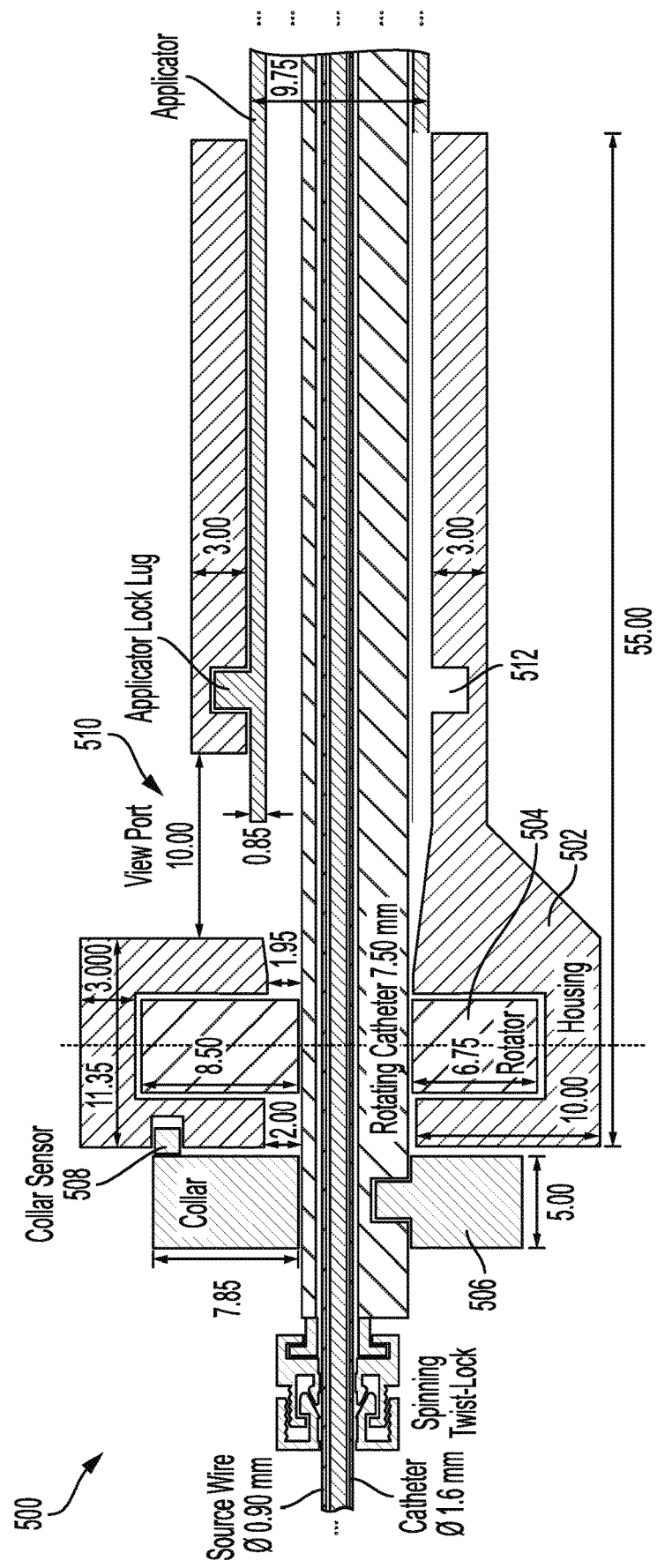
FIG. 5 illustrates a sagittal view of an exemplary apparatus as disclosed herein.

FIG. 5 illustrates a sagittal view of a drive system 500. The drive system 500 can be used with the apparatus 100 of FIG. 1 and the apparatus 200 of FIGS. 2A-2E. In an aspect, the drive system 500 can have a housing 502, a rotator 504, a collar 506, a collar sensor 508 attached to the housing 502, a view port 510, an applicator lock lug 512. The rotator 504 can be coupled with a rotating catheter to rotate the catheter. The lock lug can affix the housing to the applicator. Motors 514 (FIG. 6) can effect rotation of the rotators. The rotator can engage the catheter, for example, via frictional engagement or other means apparent to one skilled in the art, to rotate the catheter, thereby driving the catheter rotationally and longitudinally via the threaded engagement between the applicator and the catheter. Optionally, the drive system 500 can comprise two motors for the purposes of redundancy.

As the catheter rotates, it can travel longitudinally. The collar can indicate when the catheter is fully inserted into the applicator. That is, the collar can be positioned at a select distance from the end of the catheter, wherein the longitudinal position of the catheter when the collar reaches the collar sensor corresponds to the insertion distance at which the catheter extends to the distal end of the applicator (or to a select distance from the distal end of the applicator). When the catheter reaches the distal end of the applicator or the select distance from the distal end of the catheter, the collar can bias against the collar sensor, thereby causing the drive system to stop rotation once the catheter reaches a select longitudinal position. That is, the collar sensor can comprise a momentary switch that, when depressed, causes the motors to stop. For example, in one embodiment, the collar sensor can be a switch in communication with a controller (as further disclosed herein), wherein upon receiving a signal from the collar sensor, the controller can stop rotation of the motors. In this way, the collar and collar sensor can cooperate to limit the axial distance of travel of the catheter.

A spinning twist lock can couple the afterloader of the catheter to the rotating catheter so that the afterloader of the catheter can remain rationally stationary as the rotating catheter rotates.

Figure 6:
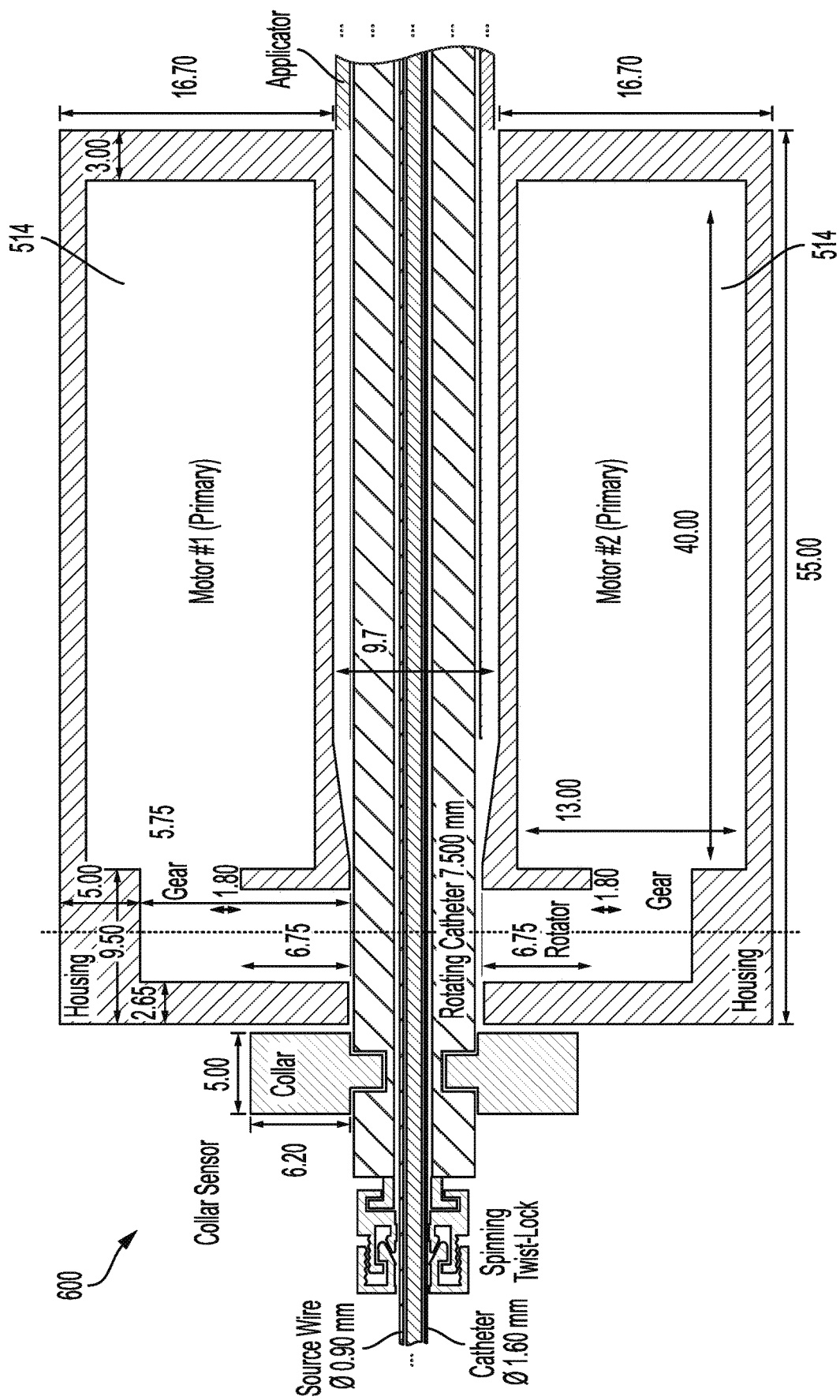
FIG. 6 illustrates a coronal view of an exemplary apparatus as disclosed herein.

FIG. 6 illustrates a coronal view of a drive system 600. The drive system 600 can be used with the apparatus 100 of FIG. 1 and the apparatus 200 of FIGS. 2A-2E. In an aspect, the drive system 500 and the drive system 600 are different views of the same system. In an aspect, the drive system 600 can have a house, a rotator, a collar, and a first and a second motor. The first and second motor can be coupled to the rotator via a gear associated with each respective motor. The rotator can be coupled with a rotating catheter to rotate the catheter.

Figure 7:
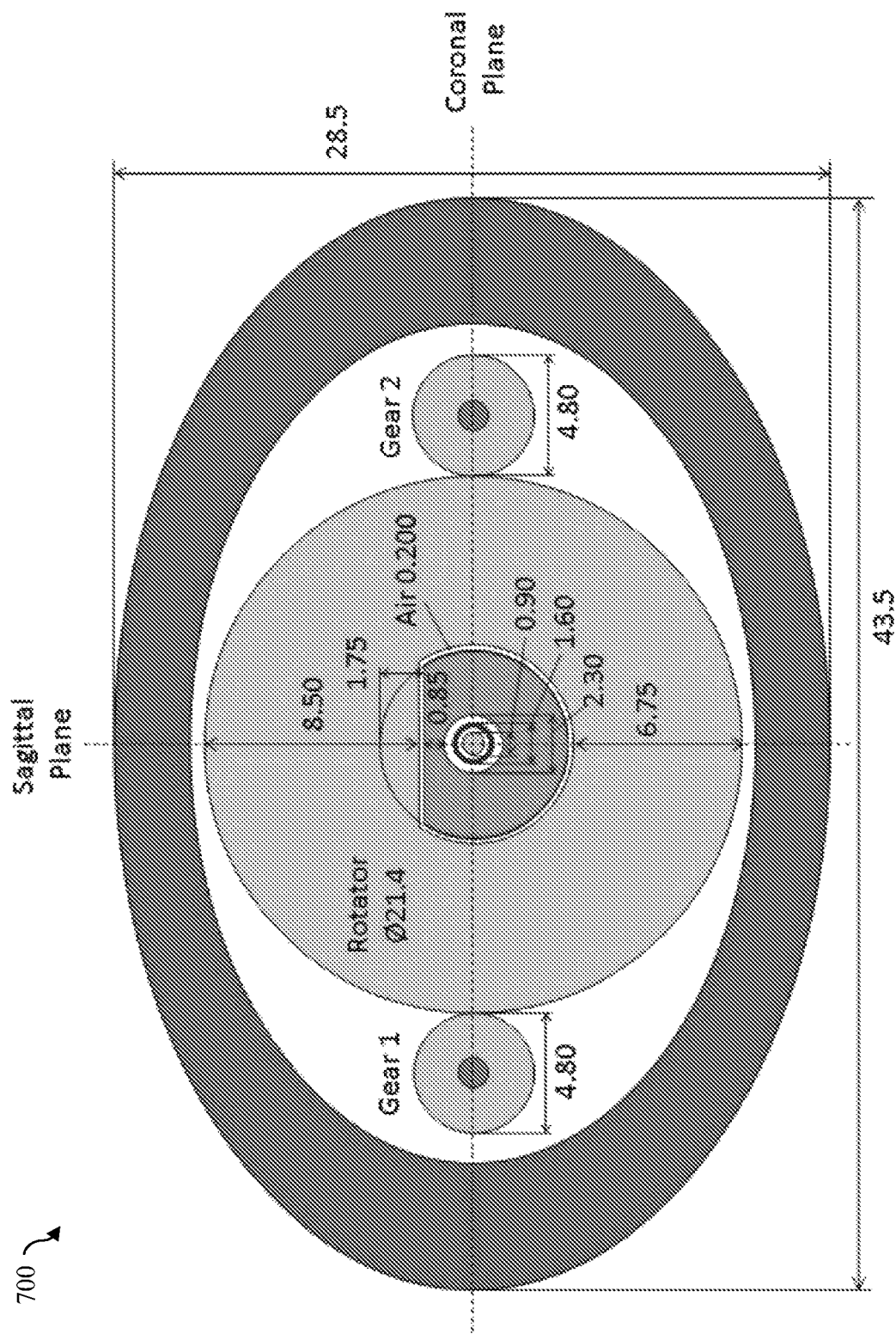
FIG. 7 illustrates an axial view of an exemplary apparatus as disclosed herein.

FIG. 7 illustrates an axial view of a drive system 700. The drive system 700 can be used with the apparatus 100 of FIG. 1 and the apparatus 200 of FIGS. 2A-2E. In an aspect, the drive system 500, the drive system 600, and the drive system 700 are different views of the same system. In an aspect, the drive system 700 can have a first gear, a second gear, a rotator, and a housing.

FIG. 10 is a flowchart of an exemplary method 1000 in which a rotating shield brachytherapy apparatus is assembled. The rotating brachytherapy apparatus can be the apparatus described in FIGS. 1 and/or 2.

FIG. 11 is a flowchart of an exemplary method 1100. At step 1110, a rotating shield brachytherapy apparatus is used. The rotating shield brachytherapy apparatus can be the apparatus described in FIGS. 1 and/or 2. At least a portion of the rotating shield brachytherapy apparatus can be inserted into a patient at a target volume. An afterloader can deliver a radiation source to a position within the lumen of the rotating catheter. The drive system can rotate the catheter with respect to the applicator to control delivery of RSBT. The RSBT apparatus can then be removed from the patient.

The following steps describe an exemplary/optional method for using a treatment planning system (TPS) and the disclosed apparatus to deliver RSBT for a cervical cancer patient.

(1) The applicator can be placed in the patient as well as an additional ring applicator component, ovoid applicator components, and/or supplementary interstitial brachytherapy needles, optionally under image guidance using a system such as ultrasound. The applicator can be positioned, for example, in the uterus of the patient. The applicator can be secured in position to the patient table so that it stays in position throughout treatment.

(2) Images of the patient anatomy and applicators can be obtained using CT or MRI.

(3) Images from (2) can be imported into the primary TPS (e.g., Varian BrachyVision, Elekta Oncentra, or Eckert & Ziegler SagiPlan) associated with the afterloader or contour-generating software, and physician contours target volumes (e.g. HR-CTV) and organs-at-risk.

(4) Contours can be imported into the primary TPS, and a physicist or a physician can reconstruct applicator positions.

(5) Contours and applicator positions can be exported from the primary TPS and imported into the RSBT TPS.

(6) an RSBT treatment plan can be generated using the RSBT TPS. The treatment plan can optionally comprise, without limitation, location of radiation exposure, duration of radiation exposure, and type of radiation exposure defined, for example, by the type of shield (e.g., 45 degree or 180 degree window) used.

(7) Physician can approve the RSBT treatment plan.

(8) Patient-specific quality assurance can be performed.

(9) Dwell position and dwell time instructions for all applicators can be exported to the afterloader, and RSBT rotating catheter instructions can be exported for the RSBT drive mechanism.

(10) A rotating catheter can be physically inserted into the applicator without the collar;

(11) The drive mechanism can be placed over the rotating catheter such that the D-cross sections in the rotating catheter and rotator align.

(12) The drive mechanism can be locked in place on the applicator.

(13) The collar can be attached to the rotating catheter.

(14) The drive mechanism can be engaged, causing the rotating catheter to proceed via helical motion (i.e., simultaneous rotation and translation) to the distal end of the applicator.

(15) The collar can reach the collar sensor, causing the drive mechanism to stop, stopping the rotating catheter at its distal-most location in the applicator.

(16) An afterloader-dependent multi-purpose catheter can be inserted into the rotating catheter and fixed in place with the spinning twist lock, or an integrated catheter can be connected between the afterloader and the rotating catheter.

(17) Other catheters from the afterloader can be connected to the associated needles and applicator components (e.g. ovoids or ring), as needed.

(18) Pre-delivery quality assurance checks can be performed by the clinical staff.

(19) RSBT can be delivered as follows:

(19.A) A radiation source can be moved to a shield, or shield-free, position in rotating catheter.

(19.B) The drive mechanism can engage, moving rotating catheter helically through applicator, with time spent at each position along the helix dictating the intensity of the radiation emitted at the corresponding position and direction.

(19.C) The radiation source can be retracted out of the rotating catheter, optionally, to an afterloader.

(19.D) If the treatment is complete; the method can proceed to step (20), otherwise go to step (19.E).

(19.E) The drive mechanism can advance the rotating catheter to the distal end of the applicator, and the method can return to step (19A). Alternatively, the rotating catheter can be removed from the applicator, and a second rotating catheter can be inserted and advanced to the distal end of the applicator, and the method can return to step (19A).

(20) A post-treatment brachytherapy processes can be completed.

Figure 12:
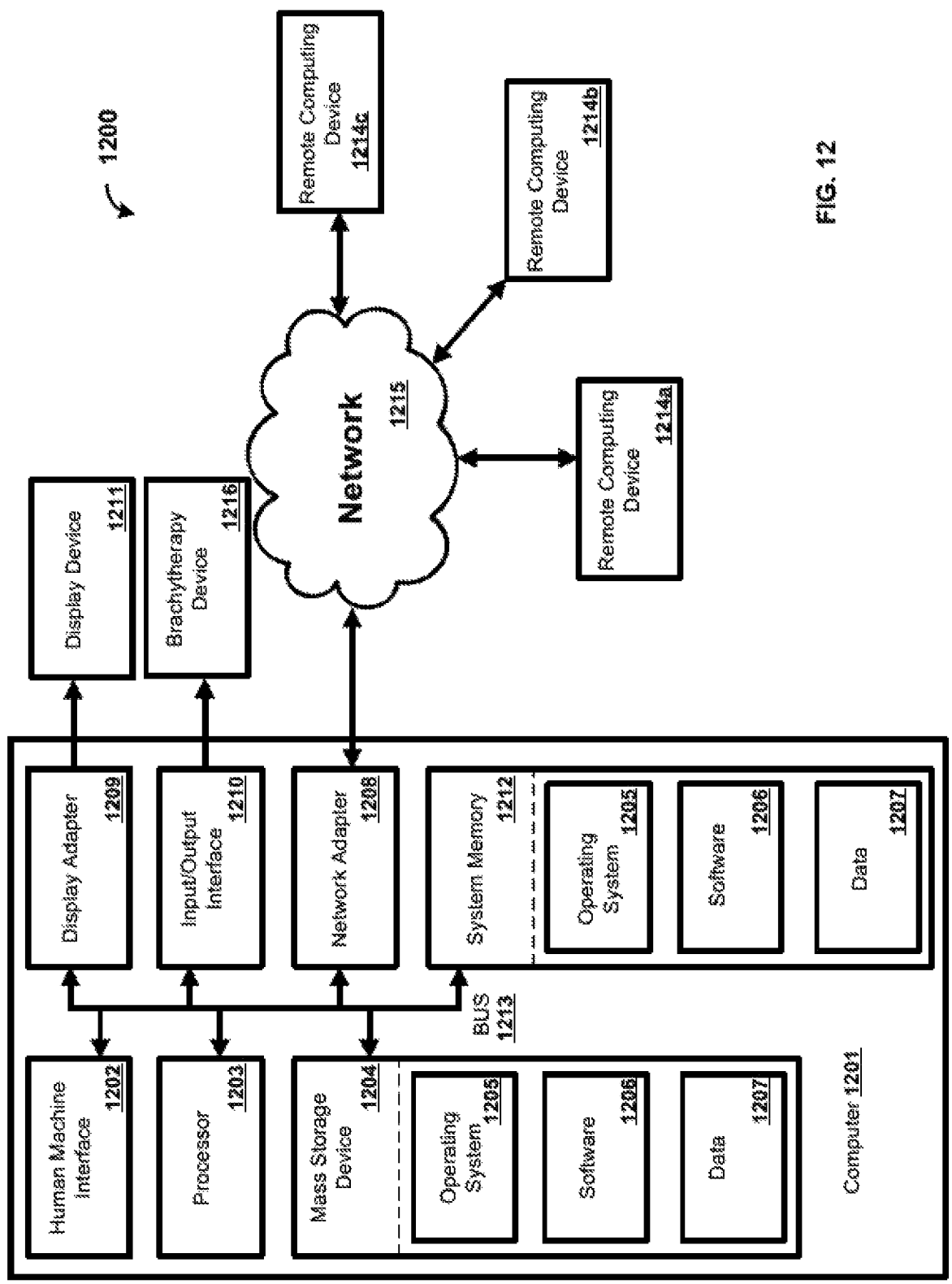
FIG. 12 is a block diagram of an exemplary computing device as disclosed herein.

FIG. 12 is an exemplary system 1200 for controlling and/or assembling an RSBT apparatus. The computer 1201 may comprise one or more processors 1203, a system memory 1212, and a bus 1213 that couples various system components including the one or more processors 1203 to the system memory 1212. In the case of multiple processors 1203, the computer 1201 may utilize parallel computing.

The bus 1213 is one or more of several possible types of bus structures, including a memory bus or memory controller, a peripheral bus, an accelerated graphics port, or local bus using any of a variety of bus architectures.

The computer 1201 may operate on and/or comprise a variety of computer readable media (e.g., non-transitory). The readable media may be any available media that is accessible by the computer 1201 and may include both volatile and non-volatile media, removable and non-removable media. The system memory 1212 has computer readable media in the form of volatile memory, such as random access memory (RAM), and/or non-volatile memory, such as read only memory (ROM). The system memory 1212 may store data such as the data 1207 and/or program modules such as the operating system 1205 and the software 1206 that are accessible to and/or are operated on by the one or more processors 1203.

The computer 1201 may also have other removable/non-removable, volatile/non-volatile computer storage media. FIG. 7 shows the mass storage device 1204 which may provide non-volatile storage of computer code, computer readable instructions, data structures, program modules, and other data for the computer 1201. The mass storage device 1204 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1204, such as the operating system 1205 and the software 1206. Each of the operating system 1205 and the software 1206 (or some combination thereof) may have elements of the program modules and the software 1206. The data 1207 may also be stored on the mass storage device 1204. The data 1207 may be stored in any of one or more databases known in the art. Such databases may be DB2®, Microsoft® Access, Microsoft® SQL Server, Oracle®, mySQL, PostgreSQL, and the like. The databases may be centralized or distributed across locations within the network 1215.

A user may enter commands and information into the computer 1201 via an input device (not shown). Examples of such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 1203 via a human machine interface 1202 that is coupled to the bus 1213, but may be connected by other interface and bus structures, such as a parallel port, game port, an IEEE 1394 Port (also known as a Firewire port), a serial port, network adapter 1208, and/or a universal serial bus (USB).

The display device 1211 may also be connected to the bus 1213 via an interface, such as the display adapter 1209. It is contemplated that the computer 1201 may have more than one display adapter 1209 and the computer 1201 may have more than one display device 1211. The display device 1211 may be a monitor, an LCD (Liquid Crystal Display), light emitting diode (LED) display, television, smart lens, smart glass, and/or a projector. In addition to the display device 1211, other output peripheral devices may be components such as speakers (not shown) and a printer (not shown) which may be connected to the computer 1201 via the Input/Output Interface 1210. Any step and/or result of the methods may be output (or caused to be output) in any form to an output device. Such output may be any form of visual representation, including, but not limited to, textual, graphical, animation, audio, tactile, and the like. The display device 1211 and computer 1201 may be part of one device, or separate devices.

A Brachytherapy device 1215 can be connected to the computer 1201 via the Input/Output Interface 1210. In an aspect, the computer 1201 can control operation of the Brachytherapy device 1215 (e.g., the Brachytherapy device of FIGS. 1 and 2). In another aspect, the computer 1201 can control assembling the Brachytherapy 1215.

The computer 1201 may operate in a networked environment using logical connections to one or more remote computing devices 1214a,b,c. A remote computing device may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device, and so on. Logical connections between the computer 1201 and a remote computing device 1214a,b,c may be made via a network 1215, such as a local area network (LAN) and/or a general wide area network (WAN). Such network connections may be through the network adapter 1208. The network adapter 1208 may be implemented in both wired and wireless environments. Such networking environments are conventional and commonplace in dwellings, offices, enterprise-wide computer networks, intranets, and the Internet.

Application programs and other executable program components such as the operating system 1205 are shown herein as discrete blocks, although it is recognized that such programs and components reside at various times in different storage components of the computing device 1201, and are executed by the one or more processors 1203 of the computer. An implementation of the software 1206 may be stored on or sent across some form of computer readable media. Any of the described methods may be performed by processor-executable instructions embodied on computer readable media.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

EXPERIMENTAL EXAMPLES

Figure 8:
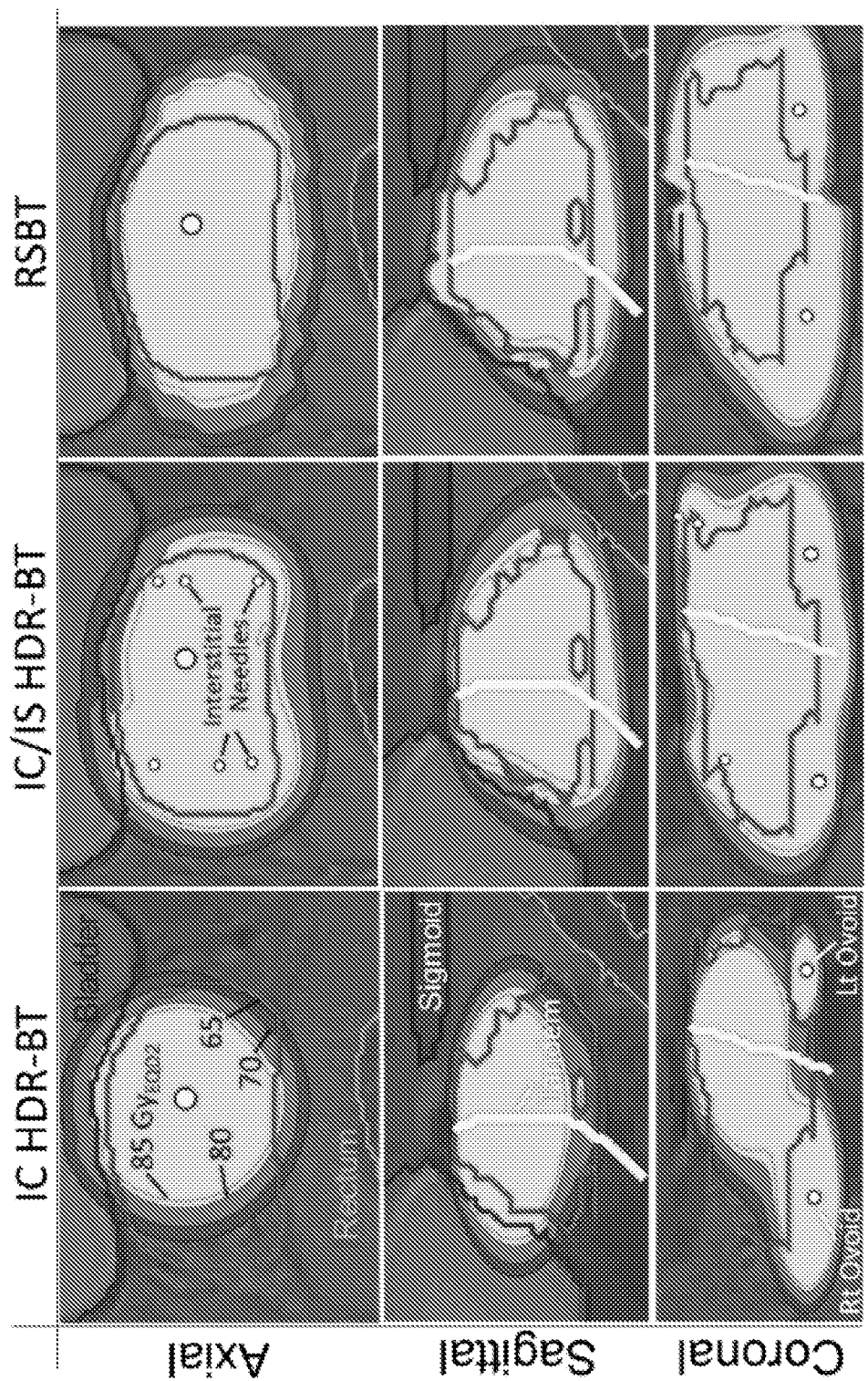
FIG. 8 illustrates dose distributions using different brachytherapy techniques.

FIG. 8 illustrates dose distributions 800 using different brachytherapy techniques. The IC and IC/IS HDR-BT calculations can be configured based on an $^{192}$Ir source. The RSBT calculations can be configured based on a $^{169}$Yb source, a 45° shield emission angle, and 8% shield transmission. In an aspect, the doses can be calculated using equivalent dose in 2 Gy fractions with $\alpha/\beta$ values of 10 Gy for the HR-CTV and 3 Gy for bladder, rectum, and sigmoid colon.

Figure 9:
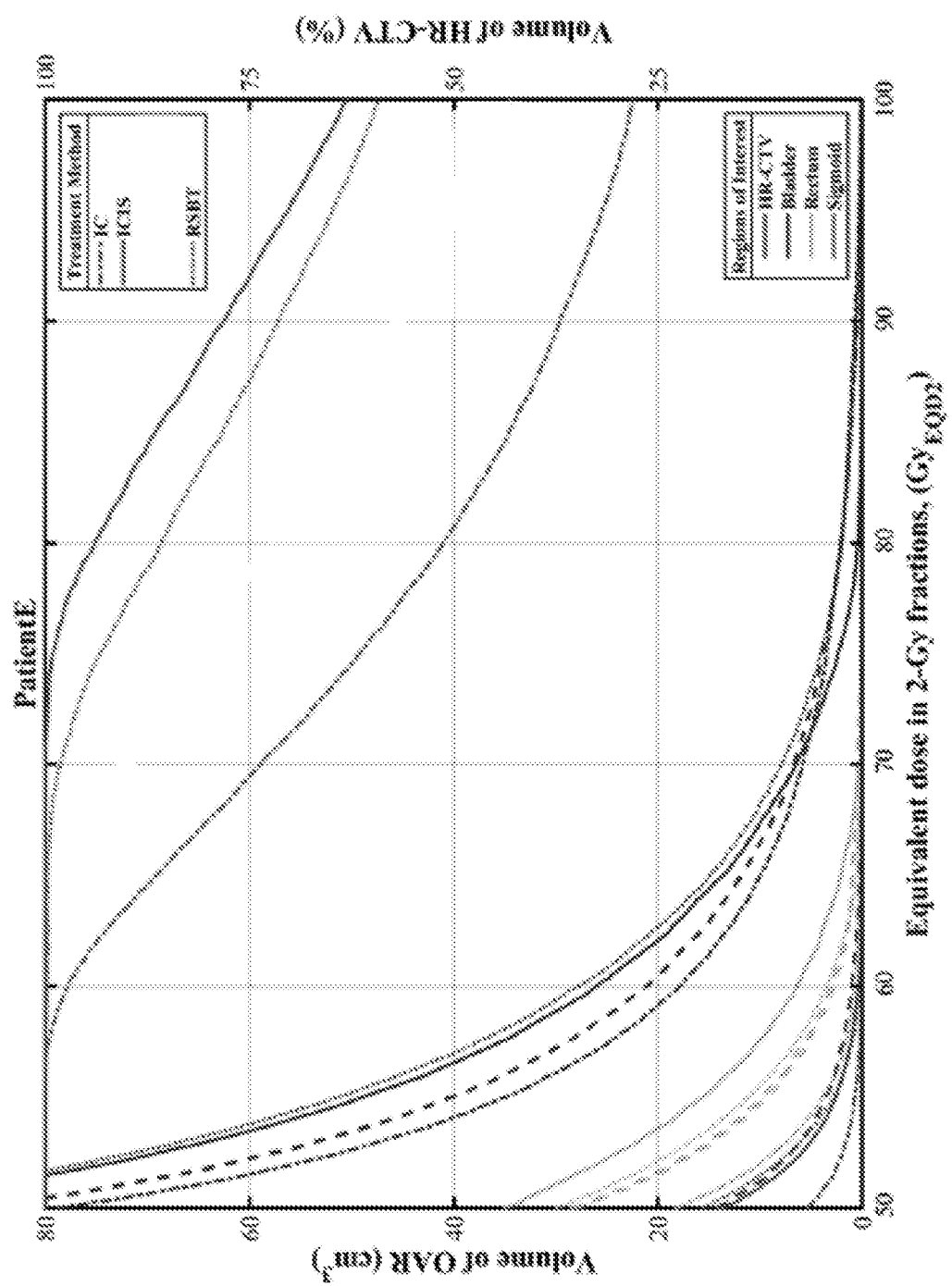
FIG. 9 is a graph showing dose-volume histograms for different brachytherapy techniques.

FIG. 9 Dose-volume histograms for IC HDR-BT, IC/IS HDR-BT, and RSBT. The dose-volume histograms can include doses from both brachytherapy and 44 $Gy_{EQD2}$ (25 fractions of 1.8 Gy each) from external beam radiation therapy. In an aspect, the doses were determined by escalation in which dwell times were scaled up until one of the tolerance doses of bladder, rectum, or sigmoid colon were reached. The HR-CTV $D_{90}$-values (minimum dose delivered to the hottest 90% of the HR-CTV in EQD2) of RSBT are equivalent to or higher than IC/IS HDR-BT.

In an aspect, the apparatus described herein can be designed to use wire-mounted, afterloader-controlled radioactive isotope sources instead of a miniature x-ray tube. Centers that currently deliver HDR-BT with conventional isotope-based afterloaders can deliver RSBT with the apparatus described herein without overcoming the impediment of purchasing and maintaining an additional x-ray tube based afterloader and the associated consumables.

In an aspect, the apparatus described herein can be designed to be used either as an integrated system with Food and Drug Association (FDA) approved HDR-BT afterloaders supplied by established vendors or as a startup company product used in combination with existing afterloaders but without official integration. Thus, the present apparatus provides flexibility and is not dependent on a single type of afterloader.

In an aspect, the apparatus described herein can be mechanically simpler than conventional brachytherapy devices, which can result in minimizing staff time and interaction required for treatment delivery.

Unless otherwise indicated, dimensions disclosed herein and shown in the Figures should be understood to be optional aspects.

EXEMPLARY ASPECTS

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A rotating shield brachytherapy (RSBT) apparatus comprising: a radiation source; a drive assembly; at least one catheter having an outer surface and opposed proximal and distal end portions and a longitudinal axis extending along a length of the catheter, wherein the distal end portion of the catheter comprises one or more radiation shields and is configured to receive the radiation source, and wherein the drive assembly is configured to engage the proximal end portion of the catheter to selectively rotate the catheter about the longitudinal axis; and an applicator having an inner surface, an outer surface, and a central axis along a length of the applicator, wherein the inner surface of the applicator defines a bore configured to receive at least a portion of the catheter, and wherein, upon receipt of the catheter within the bore of the applicator and rotation of the catheter by the drive assembly, the inner surface of the applicator is configured to engage the outer surface of the catheter in a manner sufficient to cause advancement of the catheter in a distal direction along the length of the applicator.

Aspect 2: The RSBT apparatus of aspect 1, wherein the one or more radiation shields comprise radiation-blocking material.

Aspect 3: The RSBT apparatus of aspect 2, wherein the one or more shields define at least one radiation window that allows radiation to exit the catheter.

Aspect 4: The RSBT apparatus of any one of the preceding aspects, wherein the distal end portion of the catheter comprises at least one axial position along longitudinal axis of the catheter at which no radiation shield is present.

Aspect 5: The RSBT apparatus of any one of the preceding aspects, wherein the inner surface of the applicator and the outer surface of the catheter are at least partially helically threaded, and wherein helically threaded portions of the inner surface of the applicator are configured to complementarily engage helically threaded portions of the outer surface of the catheter to permit advancement of the catheter in a distal direction along the length of the applicator.

Aspect 6: The RSBT apparatus of any one of the preceding aspects, wherein the applicator is at least partially curved.

Aspect 7: The RSBT apparatus of aspect 6, wherein the applicator has opposed proximal and distal end portions, a central portion positioned axially between the proximal and distal end portions, and a curved portion positioned axially between the central portion and the distal end portion, and wherein the bore of the applicator has a variable diameter that increases within the curved portion.

Aspect 8: The RSBT apparatus of aspect 7, wherein the distal end portion of the catheter is sufficiently flexible to traverse the curved portion of the applicator and sufficiently rigid to transfer rotational motion to the one or more radiation shields.

Aspect 9: The RSBT apparatus of any one of aspects 1-5, wherein the applicator is straight or substantially straight.

Aspect 10: The RSBT apparatus of any one of the preceding aspects, wherein the catheter defines a lumen that is configured to receive the radiation source, and wherein the lumen is radially offset from the longitudinal axis of the catheter.

Aspect 11: The RSBT apparatus of any one of aspects 1-9, the catheter defines a lumen that is configured to receive the radiation source, and wherein the lumen is aligned or substantially aligned with the longitudinal axis of the catheter.

Aspect 12: The RSBT apparatus of any one of the preceding aspects, wherein the drive assembly is configured for attachment to a proximal end portion of the applicator.

Aspect 13: The RSBT apparatus of aspect 11 or aspect 12, wherein the drive assembly comprises a locking mechanism for the catheter that prevents longitudinal motion and allows rotational motion of the catheter.

Aspect 14: The RSBT apparatus of any one of the preceding aspects, wherein the drive assembly comprises one or more rotational motors that are mechanically coupled to the catheter.

Aspect 15: The RSBT apparatus of aspect 14, wherein the one or more rotational motors comprises a plurality of rotational motors, and wherein at least one rotational motor of the plurality of rotational motors is redundant.

Aspect 16: The RSBT apparatus of any one of the preceding aspects, further comprising a second catheter coupled to an afterloader, wherein the catheter defines a lumen that is configured to receive the radiation source, and wherein the second catheter and afterloader are configured to deliver the radiation source to the lumen of the catheter.

Aspect 17: The RSBT apparatus of any one of the preceding aspects, further comprising an afterloader, and wherein the catheter defines a lumen that is directly connected to the afterloader and configured to receive the radiation source through the afterloader.

Aspect 18: The RSBT apparatus of any one of the preceding claims, wherein the applicator is an interstitial applicator.

Aspect 19: The RSBT apparatus of any one of aspects 1-18, wherein the applicator is an intracavitary applicator.

Aspect 20: The RSBT apparatus of any one of the preceding aspects, wherein the applicator comprises one or more optically transparent or translucent portions.

Aspect 21: The RSBT apparatus of aspect 20, wherein the optically transparent or translucent portions of the applicator comprise internal or external markings that configured to permit measurement of depth and/or angular location of the catheter.

Aspect 22: The RSBT apparatus of aspect 20 or aspect 21, wherein the optically transparent or translucent potions comprise internal or external markings that are configured to permit measurement of an axial location of the catheter and/or a radiation source wire within the catheter.

Aspect 23: The RSBT apparatus of any one of the preceding aspects, wherein the at least one catheter comprises a plurality of catheters, wherein each catheter comprises one or more radiation shields.

Aspect 23A: The RSBT apparatus of aspect 23, wherein each catheter of the plurality of catheters is configured for selective engagement and disengagement with the applicator to permit sequential use of multiple catheters of the plurality of catheters.

Aspect 24: The RSBT apparatus of aspect 2, wherein the radiation blocking material comprises a material selected from the group consisting of platinum, iridium, gold, silver, lead, tungsten, and osmium.

Aspect 25: A method of assembling an RSBT apparatus of any one of the preceding aspects.

Aspect 26: A method of using an RSBT apparatus of any one of aspects 1-24.

Aspect 27: A system comprising at least two RSBT apparatuses as in any of aspects 1-24.

What is claimed is:

1. A rotating shield brachytherapy (RSBT) apparatus comprising:
    a radiation source;
    a drive assembly;
    at least one catheter having an outer surface and opposed proximal and distal end portions and a longitudinal axis extending along a length of the catheter, wherein the distal end portion of the catheter comprises one or more radiation shields and is configured to receive the radiation source, and wherein the drive assembly is configured to engage the proximal end portion of the catheter to selectively rotate the catheter about the longitudinal axis; and
    an applicator having an inner surface, an outer surface, and a central axis along a length of the applicator, wherein the inner surface of the applicator defines a bore configured to receive at least a portion of the catheter, wherein the applicator is configured to be at least partially inserted into a patient, and wherein the drive assembly is mounted to the applicator, and
    wherein, upon receipt of the catheter within the bore of the applicator and rotation of the catheter by the drive assembly, the inner surface of the applicator is configured to engage the outer surface of the catheter in a manner sufficient to cause advancement of the catheter in a distal direction along the length of the applicator.

2. The RSBT apparatus of claim 1, wherein the one or more radiation shields comprises a radiation-blocking material selected from a group consisting of platinum, iridium, gold, silver, lead, tungsten, or osmium.

3. The RSBT apparatus of claim 1, wherein the one or more shields define at least one radiation window that allows radiation to exit the catheter.

4. The RSBT apparatus of claim 3, wherein the at least one catheter comprises a plurality of catheters, wherein each catheter comprises one or more radiation shields.

5. The RSBT apparatus of claim 1, wherein the distal end portion of the catheter comprises at least one axial position along the longitudinal axis of the catheter at which no radiation shield is present.

6. The RSBT apparatus of claim 1, wherein the inner surface of the applicator and the outer surface of the catheter are at least partially helically threaded, and wherein helically threaded portions of the inner surface of the applicator are configured to complementarily engage helically threaded portions of the outer surface of the catheter to permit advancement of the catheter in the distal direction along the length of the applicator.

7. The RSBT apparatus of claim 1, wherein the applicator has opposed proximal and distal end portions, a central portion positioned axially between the proximal and distal end portions, and a curved portion positioned axially between the central portion and the distal end portion, and wherein the bore of the applicator has a variable diameter that increases within the curved portion.

8. The RSBT apparatus of claim 7, wherein the distal end portion of the catheter is sufficiently flexible to traverse the curved portion of the applicator and sufficiently rigid to transfer rotational motion to the one or more radiation shields.

9. The RSBT apparatus of claim 1, wherein the catheter defines a lumen that is configured to receive the radiation source, and wherein the lumen is radially offset from the longitudinal axis of the catheter.

10. The RSBT apparatus of claim 1, wherein the catheter defines a lumen that is configured to receive the radiation source, and wherein the lumen is aligned or substantially aligned with the longitudinal axis of the catheter.

11. The RSBT apparatus of claim 1, wherein the drive assembly is configured for attachment to a proximal end portion of the applicator.

12. The RSBT apparatus of claim 11, wherein the drive assembly comprises a locking mechanism for the catheter that prevents longitudinal motion and allows rotational motion of the catheter.

13. The RSBT apparatus of claim 1, wherein the drive assembly comprises one or more rotational motors that are mechanically coupled to the catheter.

14. The RSBT apparatus of claim 13, wherein the one or more rotational motors comprises a plurality of rotational motors, and wherein at least one rotational motor of the plurality of rotational motors is redundant.

15. The RSBT apparatus of claim 1, further comprising a second catheter coupled to an afterloader, wherein the catheter defines a lumen that is configured to receive the radiation source, and wherein the second catheter and afterloader are configured to deliver the radiation source to the lumen of the catheter.

16. The RSBT apparatus of claim 1, further comprising an afterloader, and wherein the catheter defines a lumen that is directly connected to the afterloader and configured to receive the radiation source through the afterloader.

17. The RSBT apparatus of claim 1, wherein the applicator is an interstitial applicator.

18. The RSBT apparatus of claim 1, wherein the applicator is an intracavitary applicator.

19. The RSBT apparatus of claim 1, wherein the applicator comprises one or more optically transparent or translucent portions, wherein the optically transparent or translucent portions of the applicator comprise internal or external markings that are configured to permit measurement of depth and/or an angular location of the catheter.

20. The RSBT apparatus of claim 19, wherein the optically transparent or translucent portions comprise internal or external markings that are configured to permit measurement of an axial location of the catheter and/or a radiation source wire within the catheter.

* * * * *